United States Patent
Wang et al.

(10) Patent No.: US 10,946,021 B2
(45) Date of Patent: Mar. 16, 2021

(54) METHODS OF TREATING OR ALLEVIATING JOINT DISEASES BY ADMINISTERING AN INHIBITOR OF DISCOIDIN DOMAIN RECEPTOR 1 (DDR1)

(71) Applicant: Kaohsiung Medical University, Kaohsiung (TW)

(72) Inventors: Chau-Zen Wang, Kaohsiung (TW); Chung-Hwan Chen, Kaohsiung (TW); Liang-Yin Chou, Kaohsiung (TW); Yu Chou, Kaohsiung (TW); Mei-Ling Ho, Kaohsiung (TW); Yi-Hsiung Lin, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 16/496,666

(22) PCT Filed: Mar. 23, 2018

(86) PCT No.: PCT/CN2018/080238
§ 371 (c)(1),
(2) Date: Sep. 23, 2019

(87) PCT Pub. No.: WO2018/171726
PCT Pub. Date: Sep. 27, 2018

(65) Prior Publication Data
US 2020/0030332 A1    Jan. 30, 2020

Related U.S. Application Data

(60) Provisional application No. 62/475,397, filed on Mar. 23, 2017.

(51) Int. Cl.
| | | |
|---|---|---|
| *A61K 31/519* | (2006.01) | |
| *C07K 16/28* | (2006.01) | |
| *C12N 15/113* | (2010.01) | |
| *A61P 19/04* | (2006.01) | |
| *A61P 19/02* | (2006.01) | |

(52) U.S. Cl.
CPC ............ *A61K 31/519* (2013.01); *A61P 19/02* (2018.01); *A61P 19/04* (2018.01); *C07K 16/2851* (2013.01); *C12N 15/1138* (2013.01); *C07K 2317/76* (2013.01); *C12N 2310/11* (2013.01); *C12N 2310/14* (2013.01)

(58) Field of Classification Search
CPC ........ A61K 31/519; A61P 19/02; A61P 19/04; C12N 15/1138; C12N 2310/11; C12N 2310/14; C07K 16/2851; C07K 2317/76
See application file for complete search history.

(56) References Cited

U.S. PATENT DOCUMENTS

| | | | |
|---|---|---|---|
| 9,732,156 B2 * | 8/2017 | Adamkewicz | ............ A61P 1/00 |
| 10,370,360 B2 * | 8/2019 | Brekken | ................ A61P 11/00 |

FOREIGN PATENT DOCUMENTS

| | | |
|---|---|---|
| CN | 103965195 A | 8/2014 |
| KR | 20100060300 A | 6/2010 |
| WO | 2008021369 A2 | 2/2008 |
| WO | 2008058341 A1 | 5/2008 |
| WO | 2010062038 A2 | 6/2010 |
| WO | 2013068836 A1 | 12/2012 |
| WO | 2013074986 A1 | 5/2013 |
| WO | 2016064970 A1 | 4/2016 |

OTHER PUBLICATIONS

Borza et al., 2014, Discoidin domain receptors in disease, Matrix biology, 34, 185-192.
Gao et al., 2013, Discovery and optimization of 3-(2-)pyrazolo[1,5-a]pyrimidin-6-yl)-ethynyl)benzamides as novel selective andorally bioavailable discoidin domain receptor 1 (DDR1) inhibitors, J of Med Chem, 56, 3281-3295.
International Search Report and English translation issued for PCT/CN2018/080238.
Written Opinion issued for PCT/CN2018/080238.
Office Action issued for Taiwanese Application No. TW107109902.
Wang et al., 2012, BMP-2 collagen sponge repair the rabbit ear cartilage defects in rabbits, National Medical Frontiers of China, vol. 2, No. 2, 31 (Abstract in English).

* cited by examiner

*Primary Examiner* — Robert S Landsman
(74) *Attorney, Agent, or Firm* — Volpe Koenig

(57) ABSTRACT

The present invention relates to a use of Discoidin Domain Receptor 1 (DDR1) inhibitor in preparing a medicament for preventing or treating a joint disease. The present invention further relates to a use of DDR1 activator in preparing a medicament for preventing or treating abnormalities of endochondral ossification-related conditions.

16 Claims, 22 Drawing Sheets
(13 of 22 Drawing Sheet(s) Filed in Color)

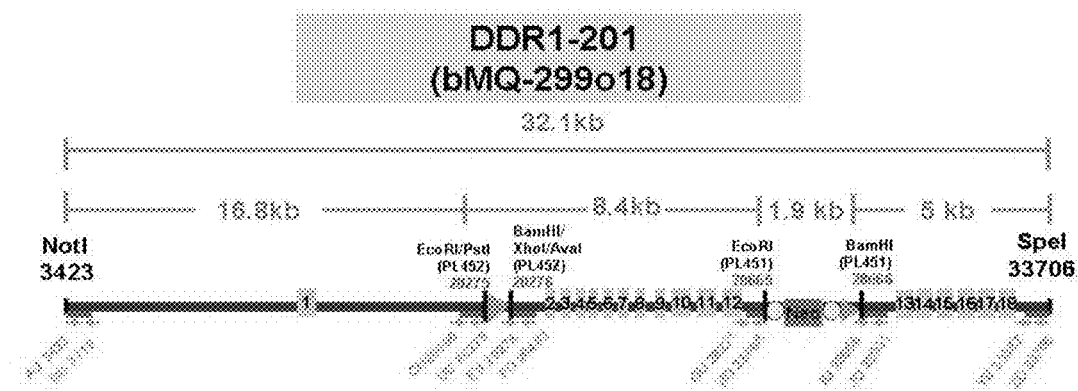
Fig. 1A
Fig. 1B
Fig. 1C
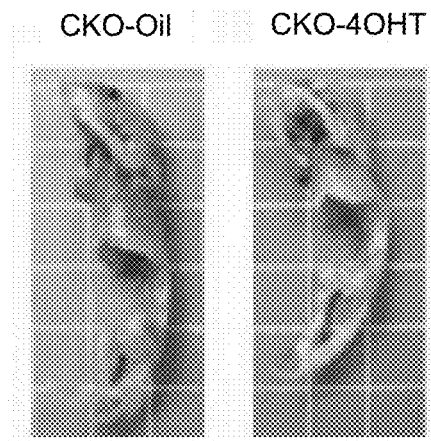
Fig. 1D

FF-4OHT

CKO-4OHT

METHODS OF TREATING OR ALLEVIATING JOINT DISEASES BY ADMINISTERING AN INHIBITOR OF DISCOIDIN DOMAIN RECEPTOR 1 (DDR1)

CROSS-REFERENCE TO RELATED APPLICATION AND CLAIM OF PRIORITY

This application is a U.S. National Stage of International Patent Application No. PCT/CN2018/080238, filed on Mar. 23, 2018, which claims the benefit of U.S. provisional application No. 62/475,397 filed Mar. 23, 2017 and is incorporated herein by reference as if fully set forth.

FIELD OF THE INVENTION

The present invention is related to inhibitors or activators of discoidin domain receptors, in particular to uses of the inhibitors or activators of the discoidin domain receptors.

BACKGROUND OF THE INVENTION

Discoidin domain receptors (DDRs) including DDR1 and DDR2 are members of receptor tyrosine kinases (RTKs) that may be stimulated by collagens. Unlike other RTKs, DDRs contain two discoidin domains in the extracellular region. DDRs are activated by a number of triple-helical collagens, which are the most abundant components of the extracellular matrix (ECM). DDR1 is widely expressed in epithelial cells in the lung, kidney, colon and brain, whereas DDR2 is primarily expressed in mesenchymal cells including fibroblasts, myofibroblasts, smooth muscle, and skeletal in kidney, skin, lung, heart, and connective tissues. Studies demonstrated that both DDR1 and DDR2 play crucial roles in fundamental cellular processes, such as proliferation, survival, differentiation, adhesion, and matrix remodeling. Deregulation of DDR1 and DDR2 was shown to be implicated in a number of diseases, including fibrotic disorders, atherosclerosis, and cancer. Although DDR1 and DDR2 belong to the same family, DDR1 and DDR2 are two different functional proteins, and the ligands responsible for activating DDR1 and DDR2 are also different. DDR1 can be activated by all types of collagens, including collagen types I to IV and collagen type VIII, whereas DDR2 can only be activated by collagen types I, III, and X. The function, use and involved signal pathway of DDR1 cannot be regarded as equivalent to those of DDR2.

Joint diseases, e.g., osteoarthritis (OA), may be chronic joint diseases characterized by degenerative lesions of articular cartilage and secondary bone hyperplasia, and commonly occur in knee joints, hip joint, lumbosacral joint, and first MIP joint with heavy load, as well as the distal interphalangeal (DIP) joints and proximal interphalangeal (PIP) joints of hands. The main cause of joint diseases like osteoarthritis is the lack of viscous synovial fluid (joint fluid) in the articular cavity, which causes the cartilage, which is supposed to act as a cushion in the joint, to be abnormally rubbed, and thus damaged and degraded. In brief, joint diseases (osteoarthritis) are caused by dysfunction, terminal differentiation and apoptosis of articular chondrocytes. Joint diseases can be classified by two types: primary or secondary. Primary joint diseases include diseases such as osteoarthrosis, degenerative arthritis, proliferative arthritis and degenerative joint disease. The primary joint diseases have no known cause, and thus those patients suffering from primary joint disease usually have no trauma, infection, history of congenital malformation, hereditary defects, or systemic metabolism and endocrine abnormalities. The secondary joint diseases (secondary osteoarthrosis) are caused by another disease or condition, such as congenital abnormalities (e.g., congenital dislocation of the hip), trauma (e.g., intra-articular fractures), articular surface irregularities (such as ischemic necrosis of the bone), joint instability (such as articular capsule or ligament relaxation), joint deformity caused by knee malalignment (such as knee varus and knee valgus). Because articular chondrocytes of adults are rarely proliferated, the reduced chondrocyte proliferation has less effect on adult joints, and the reduction in the terminal differentiation and apoptosis of articular chondrocytes is instead an important direction for the treatment of degenerative arthritis. Current treatments for joint diseases (in particular degenerative arthritis) are limited to relief of pain by non-steroidal anti-inflammatory drugs (NSAIDs), and adjuvant treatments such as oral glycosamine agent or intra-articular injection of hyaluronic acid. At present, there are no pharmacological agents capable of effectively treating joint diseases (in particular degenerative arthritis). Therefore, research and development of drugs or products that are effective in treating degenerative arthritis are very important and have high market potential.

Most of the fetal bones (such as bone of limbs, skeleton, cranial base, and so on) are formed in the way of endochondral ossification. The endochondral ossification includes not only a process similar to that of intramembranous ossification, but also the continuous growth and degradation of cartilage and the unique process of cartilage tissues being continuously replaced by bone tissues. Thus, the process of endochondral ossification is far more complicated than that of intramembranous ossification. Achondroplasia is a hereditary disease related to bone growth, mostly due to mutations in the FGFR-3 gene. For patients with achondroplasia, abnormalities of endochondral ossification cause short stature and rhizomelic shortening of (proximal) limbs. The abnormalities of endochondral ossification may also be caused by trauma, developmental disorders or other diseases. DDR1 is currently known to play an important role in bone development, but the relevant mechanisms of DDR1 in bone development and cartilage development remain unclear. Because currently, there is no drug capable of effectively treating abnormalities of endochondral ossification and achondroplasia, which can only be relieved by treating or preventing the symptoms caused by the progression of the disease, research and development of drugs or products that are effective in treating abnormalities of endochondral ossification and achondroplasia are very important and such drugs or products will have high market potential.

In view of the above, because of the defect in the prior art, the inventors have provided the present invention to effectively overcome the demerits in the prior art. The descriptions of the present invention are as follows:

SUMMARY OF EXEMPLARY EMBODIMENTS

The present invention discloses a drug for preventing or treating joint diseases and a drug for preventing or treating abnormalities of endochondral ossification. The present invention also discloses a use of a discoidin domain receptor 1 (DDR1) inhibitor in effectively relieving and treating joint diseases by suppressing DDR1 function and suppressing DDR1 pathway. In addition, the present invention also provides a use of a DDR1 activator in preventing or treating abnormalities of endochondral ossification-related conditions by activating DDR1-related pathways.

One object of this application is to provide a use of a DDR1 inhibitor in the manufacture of a medicament for preventing or treating joint diseases. Preferably, the DDR1 inhibitor is a compound of formula (I) or a pharmaceutically acceptable salt thereof:

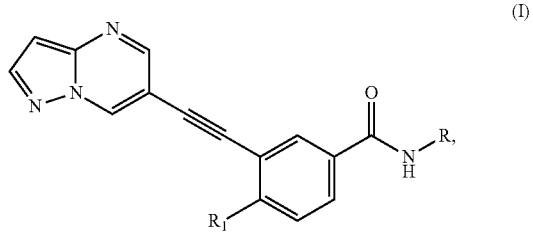

(I)

wherein R is one selected from the group consisting of

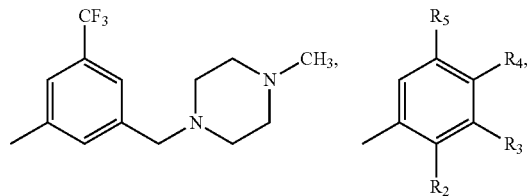

—CH(CH$_3$)$_2$, —(CH$_2$)$_3$CH$_3$, —CH$_2$CH(CH$_3$)$_2$, —C$_6$H$_{11}$ and —C$_5$H$_9$;

R$_1$ is one of —CH$_3$ and —CH$_2$CH$_3$;

R$_2$ is one selected from the group consisting of —H, —CH$_3$, —X and —OCH$_3$;

R$_3$ is one selected from the group consisting of —H, —CH$_3$, —X, —OCH$_3$, —CF$_3$, —OCH(CH$_3$)$_2$, —N(CH$_3$)$_2$,

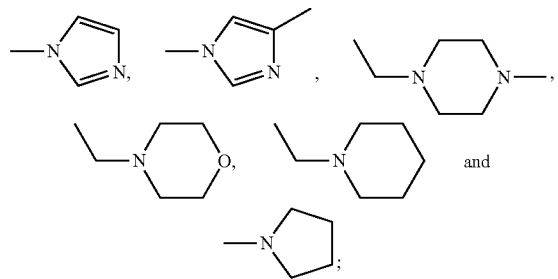

R$_4$ is one selected from the group consisting of —CH$_3$, —X, —OCH$_3$, —CF$_3$ and —H; and R$_5$ is one selected from the group consisting of —CH$_3$, —X, —OCH$_3$, —CF$_3$ and —H, where X is a halogen.

Another object of the present invention is to provide a method for preventing or treating joint diseases, wherein the method comprises administering a therapeutically effective amount of a DDR1 inhibitor to a subject in need thereof.

Another object of this application is to provide a use of a DDR1 activator in the manufacture of a medicament for preventing or treating abnormalities of endochondral ossification-related conditions. In an embodiment, the abnormalities of endochondral ossification-related conditions include achondroplasia, hypochondroplasia, thantophoric dysplasia, dwarfism, and the combinations thereof.

Another object of the present invention is to provide a pharmaceutical composition comprising a DDR1 inhibitor or a DDR1 activator.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The above embodiments and advantages of the present invention will become more readily apparent to those ordinarily skilled in the art after reviewing the following detailed descriptions and accompanying drawings:

FIG. 1A shows the synthetic vector for the chondroblast-specific transgenic mice (a1(II)-Cre/Ddr1$^{flox/flox}$ mice).

FIG. 1B shows the DNA electrophoretic pattern of the chondroblast-specific transgenic mice (a1(II)-Cre/Ddr1$^{flox/flox}$ mice) for identifying DDR1$^{flox/flox}$.

FIG. 1C shows the DNA electrophoretic pattern of the chondroblast-specific transgenic mice (a1(II)-Cre/Ddr1$^{flox/flox}$ mice) for identifying Col(II)-Cre/ERT.

FIG. 1D shows that the transgenic mice with specific deletion of DDR1 in chondroblasts (i.e., CKO mice injected with 4OHT, indicated by "CKO-4OHT") have smaller bodies compared to the control group (i.e., CKO mice injected with oil, indicated by "CKO-Oil").

In FIG. 11B, the upper two small figures have a magnification of 100 times and a scale bar of 200 µm, and the lower six small figures have a magnification of 400× and a scale bar of 50 µm.

DETAILED DESCRIPTION OF THE PREFERRED EMBODIMENTS

Figure 1E:
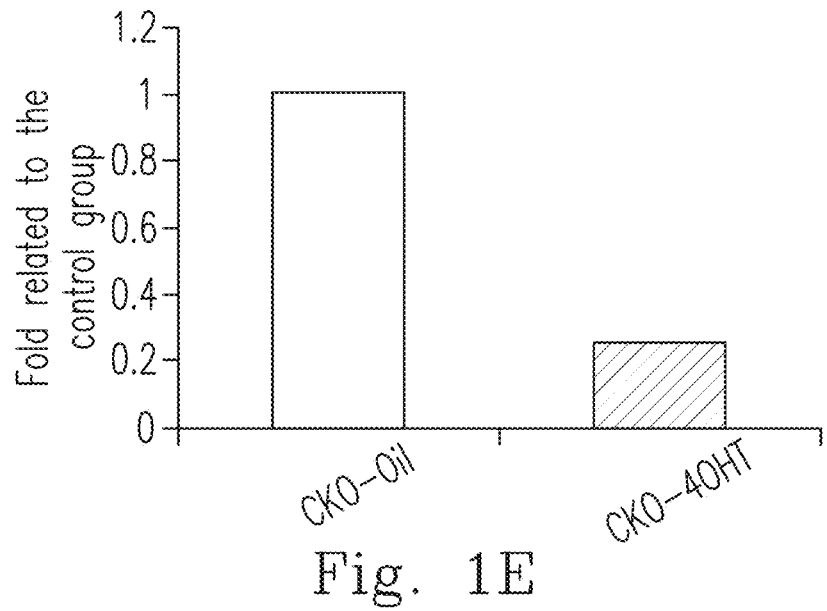
FIG. 1E shows that when compared to the control group (CKO-Oil), the DDR-1 protein level was significantly inhibited in the CKO-4OHT mice, which was shown by the western blot method and the corresponding statistical graph.

The invention provided in the present application will be fully understood by the following embodiments, so that those having ordinary knowledge in the art can achieve the invention. However, the implementation of the present invention is not limited by the following embodiments, and other embodiments can be deduced according to the spirit of the disclosed embodiments. These embodiments all fall into the scope of the present invention.

Definitions:

Unless otherwise limited in the specific examples, the following definitions can be applied to the terms used throughout the specification.

The term "compound" as used herein means any compound encompassed by the general structural formula disclosed in the present application. The present invention also comprises compounds in the form of prodrugs. The prodrugs of the compounds described in the present invention are the compounds that can be readily converted to the compounds of the present invention through chemical changes under physiological (in vivo) conditions.

The term "a halogen" refers to a substituent being a monovalent halogen selected from a group consisting of chlorine, bromine, iodine and fluorine.

The term "pharmaceutically acceptable salts" means salts of the compounds having the pharmacological activity of the parent compound.

The term "treatment" for any disease or disorder means complete or partial prevention or retard of the occurrence of the disease or the disorder or its signs or symptoms; and/or partial or complete cure or alleviation of the disease or the disorder and/or the adverse effects caused by the disorder.

The term "therapeutically effective amount" means an amount of a compound sufficient to effect treatment of a disease when the compound is administered to a patient to treat the disease. The term "therapeutically effective amount" will vary depending on the compound, the regime of administration, the disease and its severity, and the age, weight, etc. of the patient to be treated.

The term "CKO mice" means DDR1-null mice (a1(II)-Cre/Ddr1$^{flox/flox}$ mice) in which the DDR1 gene in chondroblasts is specifically knocked out. The CKO mice were obtained by crossing the offspring of a1(II)-Cre/Ddr1$^{flox/+}$ mice, which were obtained by crossing Ddr1$^{flox/flox}$ transgenic mice with a1(II)-collagen-Cre transgenic mice. In other words, the CKO mice are like mice with a knockout switch, wherein the switch can be turned on to delete DDR1 by giving 4-OHT, and thus the DDR1 gene in chondroblasts can be specifically knocked out (wherein the CKO mice with the DDR1 knocked out are referred to as "CKO-4OHT mice" or "CKO-4OHT"). In the CKO mice given oil as a placebo (hereinafter referred to as "CKO-Oil mice" or "CKO-Oil"), the switch to knock out DDR1 is unable to be turned on.

Biological Experiments

Transgenic Mice (a1(II)-Cre/Ddr1$^{flox/flox}$ Mice)

To avoid the interference limitation of the systemic Ddr1 knockout mouse, the inventors pioneered the conditional knockout of the DDR1$^{flox/flox}$ transgenic mice model using the Cre-LoxP system based on the Cre recombinase and the loxP sequences. As shown in FIG. 1A, loxP was ligated at both ends of exon 2 and exon 12 of the DDR1 locus. The targeting vector (P1253) harboring floxed Ddr1 site and the neomycin resistance (NeoR) cassette were electroporated into embryonic stein (ES) cells derived from 129P2 background mice. The ES cells containing the floxed Ddr1 allele were injected into blastocysts of C57BL/6 embryos to generate chimeric mice, and the offspring were crossed with flippase (FLP) transgenic mice to remove NeoR franked by the FLP recombinase targete (FRT) sequence. The hybrid mice were backcrossed with C57BL/6 strain (C) for 12 generations to produce Ddr1$^{flox/flox}$ mice, which were further maintained on a C57BL/6J genetic background. A1(II)collagen-Cre/-Ddr1$^{flox/flox}$ mice are chondrocytes-specific Ddr1-deficient mice. A1(II)-Cre/Ddr1$^{flox/flox}$ mice (hereinafter referred to as CKO mice), which are chondroblast-specific DDR1 knockout mice, were obtained by intercrossing the offspring of a1(II)-Cre/Ddr1$^{flox/+}$ mice, which were obtained by crossing Ddr1$^{flox/flox}$ transgenic mice with a1(II)-collagen-Cre transgenic mice (referring to FIG. 1B to FIG. 1C). Genotyping was performed via polymerase chain reaction (PCR) using tail genomic DNA. The presence of the 3'loxP site was verified by PCR using primers.

For Cre-LoxP system, the targeted integration (knockin) of loxP sites via homologous recombination (HR) and the expression of inducible Cre recombinase is required. The ligand binding domain of the estrogen receptor (ER) was fused with Cre recombinase to form a fusion protein (Cre-ER) localized in the cytoplasm. In this way, the time-specific regulation of gene recombination can be achieved by controlling the injection time of estrogen. In order to avoid interference with endogenous estrogen, a point mutation (G521R) in the ligand binding domain of human ER allows Cre-ER to respond only to the induction of exogenous synthetic estrogen (e.g., 4-hydroxytamoxifen, 4-OHT), and such Cre-ER is named as Cre-ERT. Another fusion protein (Cre-ERT2) of Cre and a mutated ligand binding domain (LBD) of human estrogen receptor ERT2 was shown to have a much higher sensitivity to 4-OHT than Cre-ERT. Cre-ERT2 has three point mutations in human ER LBD: C400V/M543A/L544A. If Cre-ERT2 is designed to locate after a tissue-specific promoter and the resultant mice are crossed with flox mice, a spatio-temporal specific knockout of a target gene can be achieved by administering 4-OHT at a specific time point. That is, a fusion protein of Cre and a mutated ligand binding domain of human estrogen receptor ERT2 is commonly used to control Cre activity by 4-OHT, which promotes CreERT2 translocation from the cytoplasm to the nucleus where the Cre recognizes and recombines loxP sites embedded in the genomic DNA. In short, 4-OHT acts like a switch that can initiate gene knockout. During the embryonic period, 4-OHT-injected mice will initiate gene knockout, and for mice without 4-OHT (i.e., mice injected with olive oil during embryonic period as the control group), no gene knockout occurred. The 4-OHT controlled gene knockout is used in the present application to assess the immediate impact of DDR1 gene loss.

I. Joint Diseases (Osteoarthritis) Can Be Prevented and Treated by Inhibiting DDR1.

1. Materials and Methods

CKO-Oil Mice and CKO-4OHT Mice 50 mg of 4-OHT powders (T5648, Sigma-Aldrich, St. Louis, Mo., USA) were dissolve in 50 μl of DMSO and shaken overnight to prepare a stock solution. The stock solution was dissolved in a mixed solution of corn oil (C8267, Sigma-Aldrich) and DMSO of 9:1 for a working concentration of 4 mg/day/kg of mouse weight. On the 21$^{st}$ day of pregnancy, 4-OHT (4 mg/day/kg of mouse weight) and progesterone (P0130, Sigma-Aldrich, 2 mg/day/kg of mouse weight) or olive oil were intraperitoneally (IP) injected into embryos of the mother mice. After the mice were born, 4-OHT (4 mg/day/kg mouse weight) or oil was intraperitoneally injected daily to the mice for one week to obtain 1-week-old CKO-4OHT mice injected with 4-OHT and the CKO-Oil mice injected with oil. Alternatively, after the mice were born, the mice were intraperitoneally injected with 4-OHT (4 mg/day/kg mouse weight) or oil for 5 consecutive days and then rested for 2 days for two or four cycles to obtain 2-week-old and 4-week-old CKO-4OHT mice injected with 4-OHT and 2-week-old and 4-week-old CKO-Oil mice injected with oil.

Anterior Cruciate Ligament Transection (ACLT) Induced Osteoarthritis (ACLT-OA)

To establish ACLT-induced OA mice, the anterior cruciate ligament transaction (ACLT) was performed on 9-week-old (adulted) mice, while the control group underwent arthrotomy (indicated by "Sham"), to investigate the role of DDR1 in chondrocytes during OA progression. Five days before the ACLT operation and 2 days after the ACLT operation, 4-OHT (Sigma-Aldrich) or olive oil/vehicle was given by the intraperitoneal injection at a dose of 4 mg/day/kg mouse weight twice for 5 consecutive days.

Immunohistochemical Staining (IHC Staining)

Immunohistochemical staining involves the process of identifying the target antigens in cells or a tissue section by exploiting the principle of antibodies being conjugated to a fluorophore or an enzyme that can catalyse a colour-producing reaction and binding specifically to antigens in biological tissues. This method can be used not only to detect the expressed amount of antigen but also to observe the position of the expressed antigen. IHC staining herein was performed by using the Impress Cruz staining system (Santa Cruz Biotechnology Inc.) as follows: The collected tibia were fixed with 10% formalin solution, decalcified with 1% formic acid solution at 4° C., embedded in paraffin, and then cut into slices having a thickness of 5 μm. Deparaffinization and rehydration were performed for the tibia slices. Antigen retrieval was performed in 2.5% of hyaluronidase (H4272, Sigma-Aldrich) and 0.1% of proteinase K (P8107S, BioLabs, New England) in 1×PBS solution for 10 min. The slices were placed in 3% hydrogen peroxide for 10 minutes at room temperature, and then cultured in IX PBS solution containing 5% bovine serum albumin (A2153, Sigma-Aldrich) at 37° C. for 1 hour to avoid non-specific binding. The primary antibody was diluted with the above solution, followed by addition of tibia slices at 4° C. overnight. The primary antibody used in this assay and its dilution ratio are as follows: anti-Ki-67 antibody, 1:250 (AB9260, Millipore); anti-Sox-9 antibody, 1:250 (AB5535, Millipore); anti-collagen type II antibody, 1:250 (ab34712, abcam); anti-collagen type X antibody, 1:250 (LB-0092, Cosmo Bio Co LTD); anti-Ddr1 antibody, 1:250 (PA5-29316, Thermo Fisher Scientific In); anti-Ihh antibody, 1:100 (TA334682, Origene); and anti-PTHrP antibody, 1:300 (ab52919, abcam). After washing with PBS, a secondary antibody diluted 1:400 was added and reacted at room temperature for 1 hour. The secondary antibody may be a peroxidase-conjugated AffiniPure Goat Anti-rabbit IgG (125510, Jackson immunoreserch) or a peroxidase-conjugated AffiniPure Goat Anti-mouse IgG (Jackson immunoreserch). The DAB substrate kit (ab64238, Abcam) was used to enhance the signal, and the slices were finally counterstained with hematoxylin and observed under a microscope.

Quantitative Real-Time PCR (RT-qPCR) Analysis

The muscles and tendons of 4 to 5 days old newborn CKO-4OHT and CKO-Oil mice were removed, and only the long bone cartilage was retained under a dissecting microscope on ice. Total RNA was extracted with TRIzol (Life Technologies) and translated into 2 mg cDNA using SuperScript II First Strand Synthesis System (Invitrogen). In quantitative real-time polymerase chain reaction (qRT-PCR), the total of 13 μl of the reaction solution contains 6.25 μl of SYBR Green Real time PCR Master Mix (Toyobo) containing 100 nM primer and 1 μl of cDNA. CFX is connected to the real-time PCR detection system (Bio-Rad) during the reaction.

Statistical Analysis

Each experiment was repeated at least three times, and the data are expressed as the means±standard error (SEM) of the combined data from each experimental replicate. Statistical significance was evaluated by a one-way analysis of variance (ANOVA), and multiple comparisons were performed using Scheffe's method. (*) and (**) indicate $p<0.05$ and $p<0.01$, respectively, both of which are considered to be significant differences.

2. CKO-Oil and the CKO-4OHT Mice Models

Figure 1F:
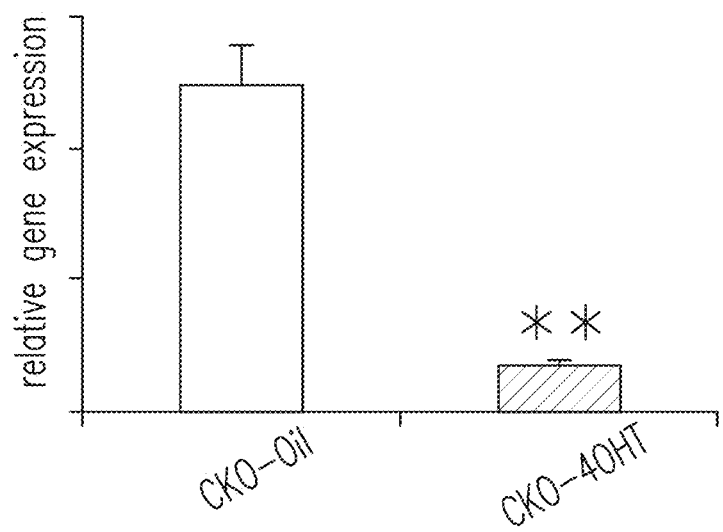
FIG. 1F shows that when compared to the control group (CKO-Oil), the gene expression of DDR-1 was significantly inhibited in CKO-4OHT mice.

To investigate whether Ddr1 deficiency affects OA progression, CKO mice injected with oil (indicated by "CKO-Oil", with normal Ddr1) and CKO mice injected with 4-OHT (indicated by "CKO-4OHT", with Ddr1 knockout) for the follow-up testing. Referring to FIGS. 1D to 1F, the gene expression and protein expression in the transgenic mice (the CKO-4OHT mice) in which the Ddr1 in chondroblasts was knocked out were inhibited and the morphology became smaller than that of the control group (the CKO-Oil mice). In addition, after staining with immunohistochemical staining (IHC), it was observed that CKO-4OHT mice with DDR1 gene knocked out did not express DDR1 (not shown in figures). Ddr1 knockout mice, which showed specific and inducible knockout of Ddr1 in chondrocytes, have phenomenons of the broadened epiphyseal plate and dwarfism, which are caused by not only the decreased chondrocytes proliferation in the epiphyseal plate, but also the significant reductions of the terminal differentiation and apoptosis of the chondrocytes, thus causing reduction of angiogenesis and the entry of osteoblasts into the epiphyseal plate, and finally the reduction of ossification.

3. Intraperitoneal Injection of 4-OHT Does Not Affect Normal Joints and the Integrity of the Articular Cartilage in the Knockout Mice Which Showed Specific and Inducible Knockout of Ddr1 In Chondrocytes.

Figure 2A:
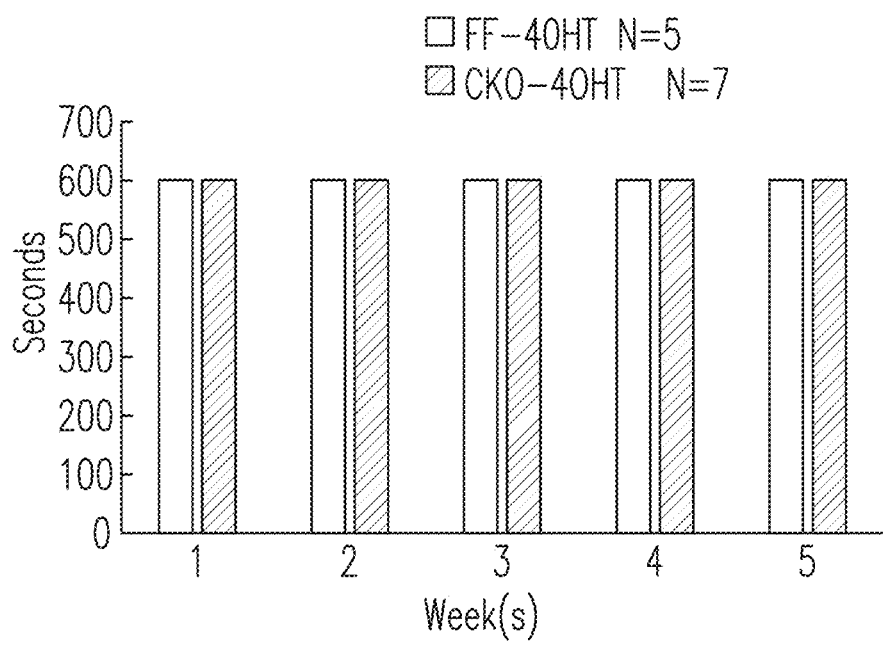
FIG. 2A shows the results of a five-week running test for the Ddr1$^{flox/flox}$ transgenic mice (the control group, expressed as "FF-4OHT") and the CKO-4OHT mice with Ddr1 deletion after intraperitoneal (IP) injection of 4-OHT.
Figure 2B:
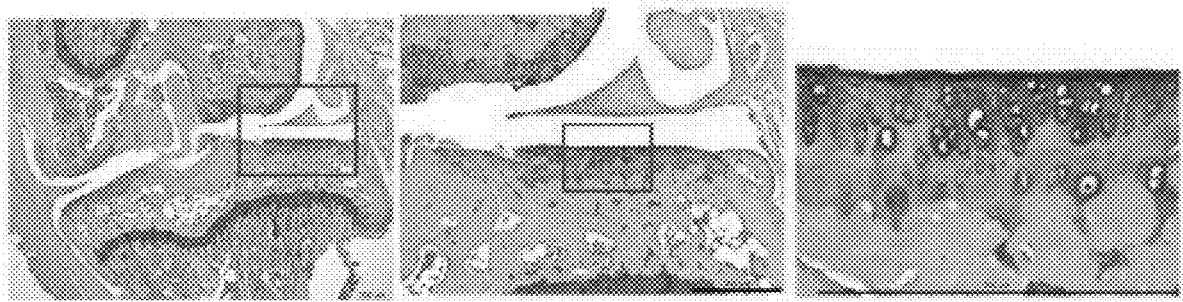
FIG. 2B shows the results of the staining by Safranin O and Fast Green in Ddr1$^{flox/flox}$ mice (the control group, expressed as "FF-4OHT") and the CKO-4OHT mice with Ddr1 deletion after IP injection of 4-OHT. Safranin O/Fast Green staining can be used to directly observe the structures of articular cartilages, subchondral bone, and bone tissue. After staining, proteoglycan is red and collagen is blue.
Figure 2B:
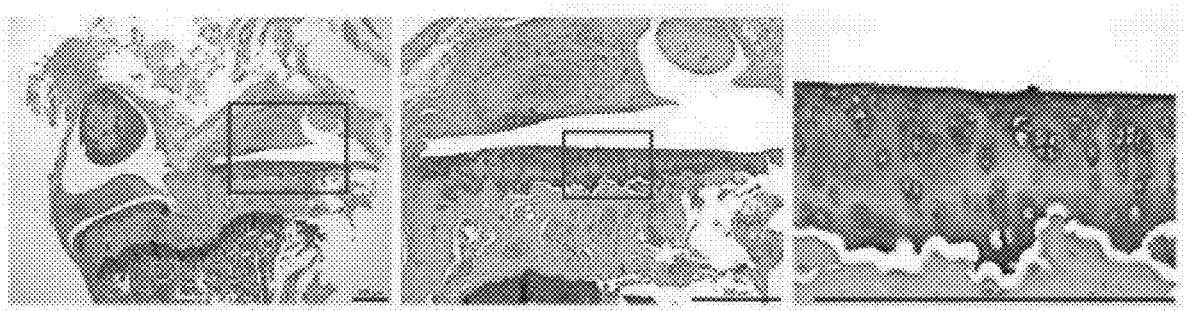

FIGS. 2A and 2B show the results of five-week running test and the results of staining with Safranin O/Fast Green in Ddr1$^{flox/flox}$ transgenic mice (the control group, expressed as "FF-4OHT") and the CKO-4OHT mice (with Ddr1 knocked out) intraperitoneally injected with 4-OHT. From the results of five-week running test, it was found that there was no significant difference between the FF-4OHT mice and the CKO-4OHT mice. From the Safranin O/Fast Green staining results in FIG. 2B, it was confirmed that the cartilage integrity in the normal joint of CKO-4OHT mice was not affected when compared with that of the tibia of Ddr1$^{flox/flox}$ transgenic mice (the control group).

4. DDR1 Can Play the Role in Protecting Articular Cartilage in ACLT-OA.

Figure 3A:
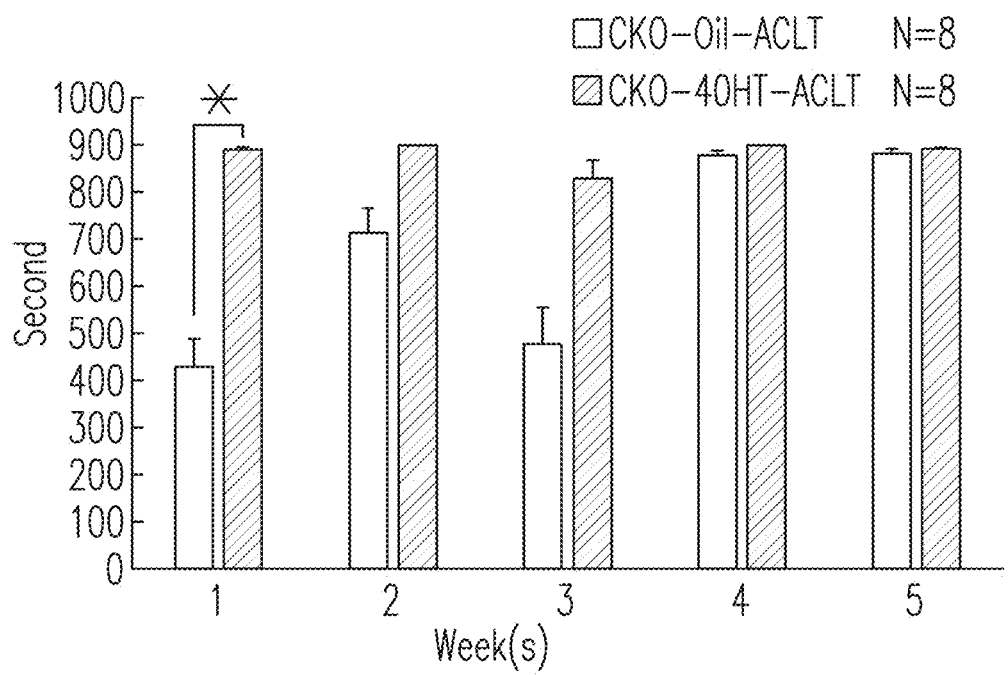
FIG. 3A shows the results of a five-week running test for the ACLT-OA/CKO mice intraperitoneally injected with oil (with normal Ddr1, indicated by "CKO-Oil-ACLT") and the ACLT-OA/CKO mice intraperitoneally injected with 4-OHT (with Ddr1 knocked out, indicated by "CKO-4OHT-ACLT").
Figure 3B:
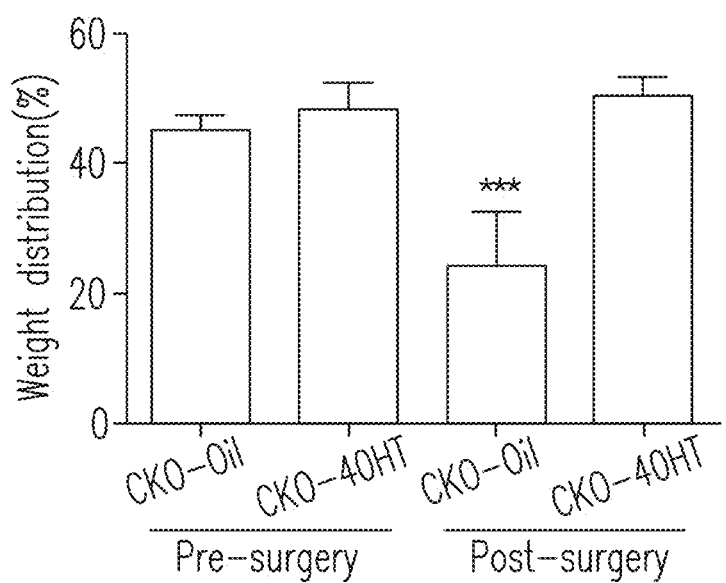
FIG. 3B shows the results of the weight-bearing for the CKO-Oil mice and the CKO-4OHT mice before and after ACLT-OA surgery.

Subsequently, the differences between ACLT-OA/CKO mice intraperitoneally injected with oil (with normal Ddr1, indicated by "CKO-Oil-ACLT") and the ACLT-OA/CKO mice intraperitoneally injected with 4-OHT (with Ddr1 knocked out, indicated by "CKO-4OHT-ACLT") in the OA processes for tibia articular cartilage were also discussed. FIG. 3A shows the results of five-week running test for the CKO-Oil-ACLT mice and the CKO-4OHT-ACLT mice. The results of this test can be used to observe the effect of surgery on mouse behavior patterns. As shown in FIG. 3A, there was a significant difference in the running behavior between the two groups of mice only in the first week, and there was no significant difference in the running behavior test in the second to fifth weeks. FIG. 3B shows the results of weight bearing for the CKO-Oil mice and the CKO-4OHT mice before and after the ACLT surgery. It can be seen from the weight-bearing test that the CKO-4OHT mice were more stable in weight-bearing ability after ACLT surgery than CKO-Oil mice (the control group). It can be seen from FIGS. 3A and 3B that DDR1 can play a role in protecting articular cartilage in osteoarthritis induced by ACLT.

Figure 4:
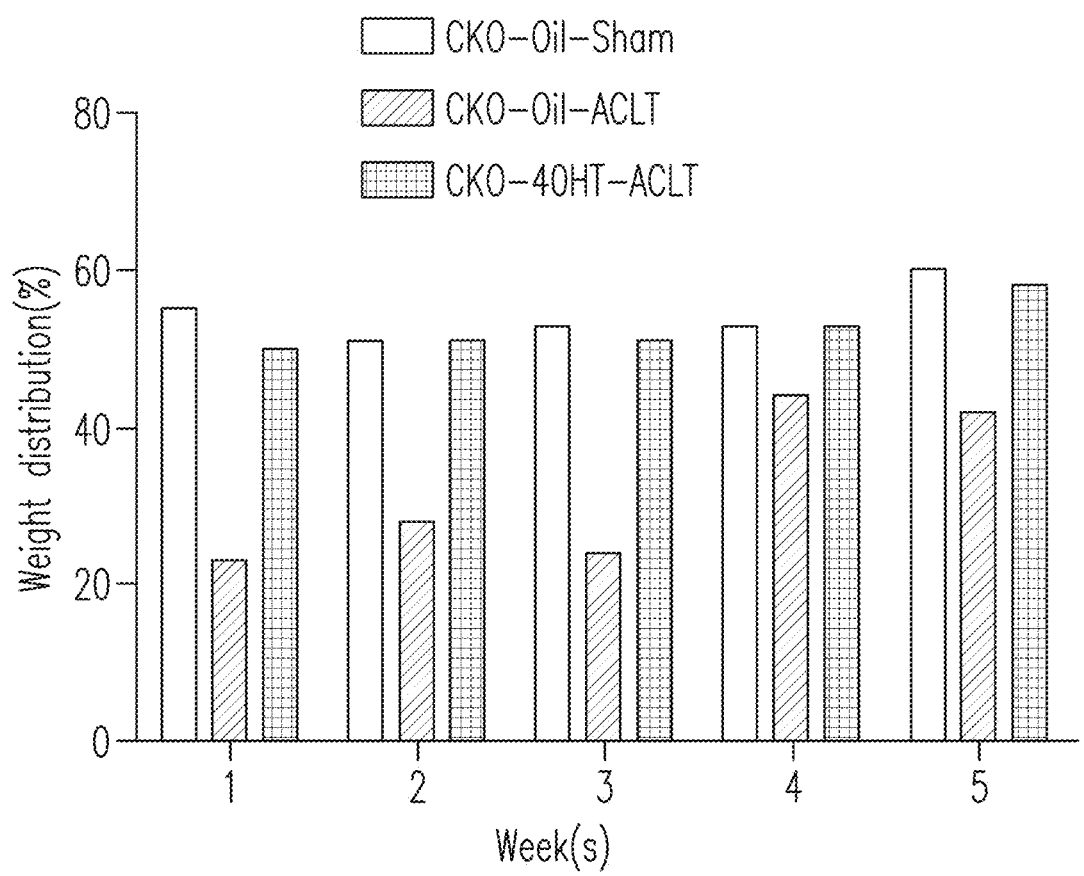
FIG. 4 shows the results of the weekly weight-bearing test from 1 week to 5 weeks after the surgery for the CKO mice intraperitoneally injected with oil (with normal Ddr1, indicated by "CKO-Oil-Sham"), the ACLT-OA/CKO mice intraperitoneally injected with oil (with normal Ddr1, indicated by "CKO-Oil-ACLT") and the ACLT-OA/CKO mice intraperitoneally injected with 4-OHT (with Ddr1 knocked out, indicated by "CKO-4OHT-ACLT").

FIG. 4 shows the results of weekly weight-bearing tests from 1 week to 5 weeks after the surgery for the CKO mice treated with arthrotomy and intraperitoneally injected with oil (with normal Ddr1, indicated by "CKO-Oil-Sham"), ACLT-OA/CKO mice intraperitoneally injected with oil (with normal Ddr1, indicated by "CKO-Oil-ACLT") and the ACLT-OA/CKO mice intraperitoneally injected with 4-OHT at 4 mg/day/kg mouse weight (with Ddr1 knocked out, indicated by "CKO-4OHT-ACLT"). The weekly weight-bearing changes were recorded from 1 week to 5 weeks after surgery. Compared to the CKO-Oil-ACLT group, the value of the weight-bearing test for the CKO-4OHT-ACLT mice was closer to that for the CKO-Oil-Sham control group. That is, when compared to the Oil group (with Ddr1), the CKO-4OHT group (without Ddr1) has more potential to effectively stabilize the function of the joints without being affected by the surgery.

Figure 5:
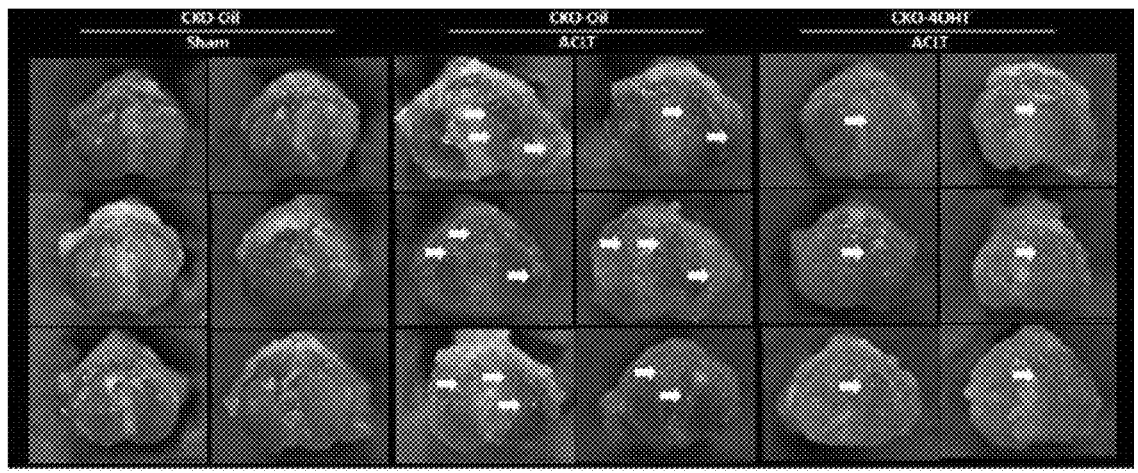
FIG. 5 shows the actual flaking of the bare joint surfaces of the CKO mice intraperitoneally injected with oil (represented by "CKO-Oil/Sham"), the ACLT-OA/CKO mice intraperitoneally injected with oil (represented by "CKO-Oil/ACLT") and the ACLT-OA/CKO mice intraperitoneally injected with 4-OHT (represented by "CKO-4OHT/ACLT") under the observation of a dissecting microscope. The white arrow in the figure marks the position of spurs.

To investigate the effects of ACLT surgery on joints, the mice were sacrificed after the fifth week of the weekly weight-bearing test and running test, and the actual wear of the bare joint surface was observed by a dissecting microscope. As shown in FIG. 5, comparing the experimental group of CKO-4OHT with the control groups injected with oil (including CKO-Oil/Sham and CKO-Oil/ACLT), on the whole, the experimental group with Ddr1 knocked out was less likely to have spurs (indicated by white arrows) and wear resulting from joint movements caused by anterior cruciate ligament transaction.

Figure 6A:
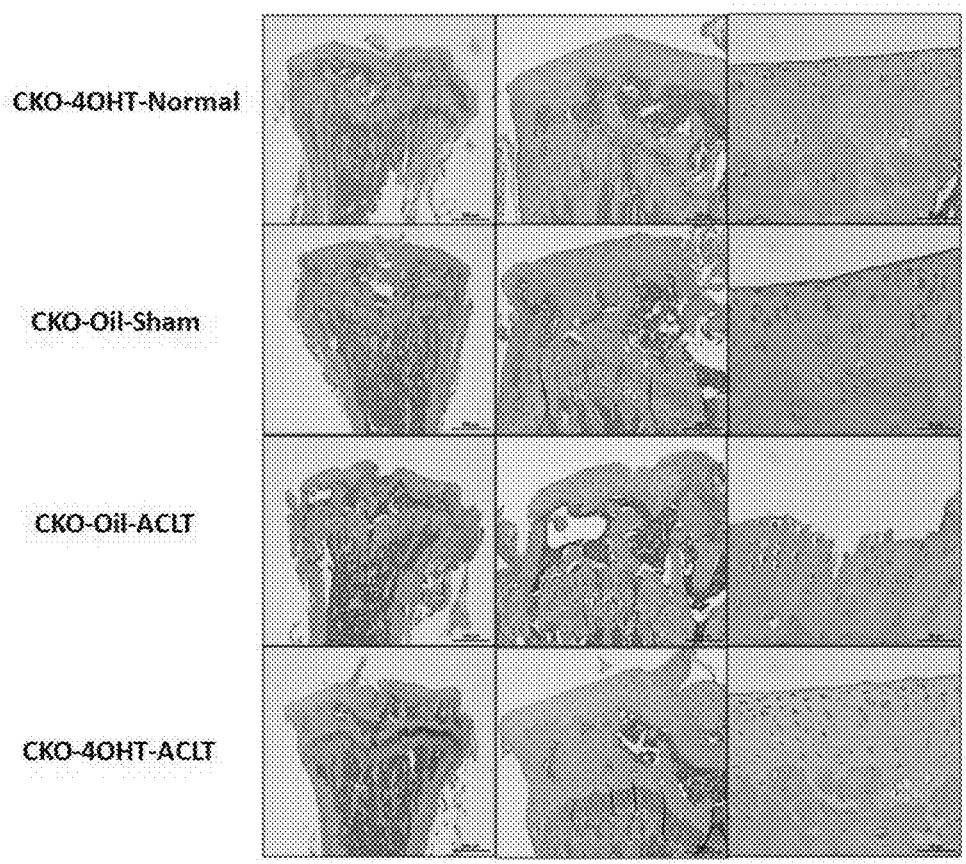
FIG. 6A shows the cartilage losses in the tissue surface in the CKO mice intraperitoneally injected with oil (represented by "CKO-Oil/Sham"), the ACLT-OA/CKO mice intraperitoneally injected with oil (represented by "CKO-Oil/ACLT"), the normal CKO mice intraperitoneally injected with 4-OHT (represented by "CKO-4OHT-Normal") and the ACLT-OA/CKO mice intraperitoneally injected with 4-OHT (represented by "CKO-4OHT/ACLT") by using hematoxylin eosin staining (H&E Stain).
Figure 6B:
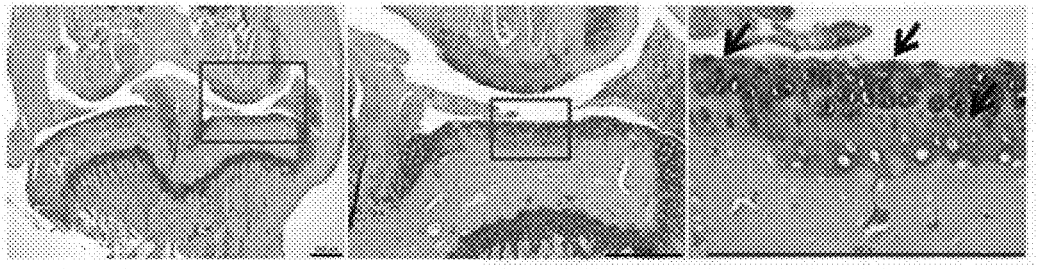
FIG. 6B shows the staining results by safranin O/Fast Green in the CKO-Oil-ACLT mice and the CKO-4OHT-ACLT mice. The arrow indicates the locations of the proteoglycan (sGAG).
Figure 6B:
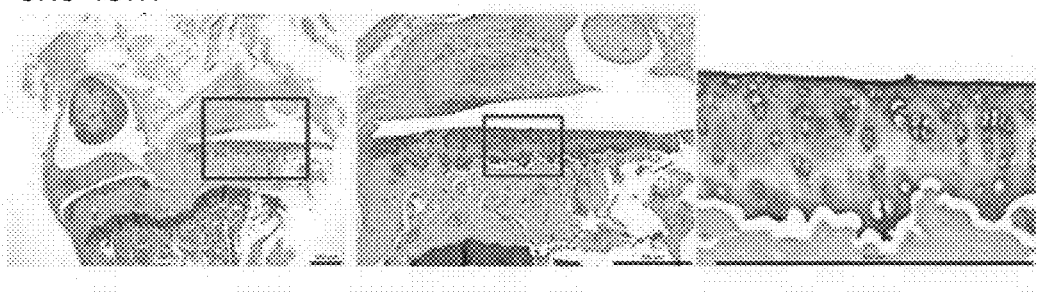

The articular cartilages of the CKO-Oil-ACLT mice and the CKO-4OHT-ACLT mice were harvested, decalcified, fixed, and embedded in paraffin for conducting Safranin O/Fast Green staining to observe the morphology differences caused by IP injection of oil and 4-OHT. As shown in FIG. 6A and FIG. 6B, based on the sliced and stained tissue samples from the CKO-4OHT-ACLT mice, the loss of proteoglycan (sGAG, as shown by the arrows in FIG. 6B), the wear and damage of the surface of joint cartilage, and the increased density of chondrocytes in adjacent areas were observed. In addition, bone spurs were present in 5/6 of the groups without treatment (i.e., the groups in which Ddr1 was not deleted). Compared with the CKO-Oil-ACLT control group, the tibia articular cartilage in the CKO-4OHT-ACLT mice group (with Ddr1 knocked out) showed less damage, indicating that the CKO-4OHT-ACLT mice group showed a tendency to effectively reduce the apoptosis of the chondrocytes.

Figure 6C:
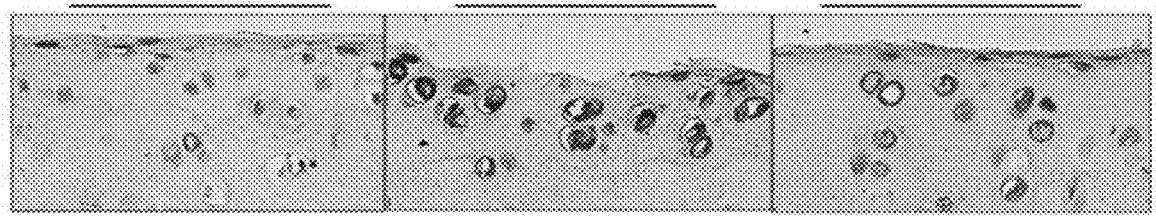
FIG. 6C shows the staining of the tibial articular cartilages of the CKO-Oil-Sham mice, the CKO-Oil-ACLT mice, and the CKO-4OHT-ACLT mice by using immunohistochemistry (IHC) staining, to observe the expression of mammalian target of rapamycin (mTOR).
Figure 6D:
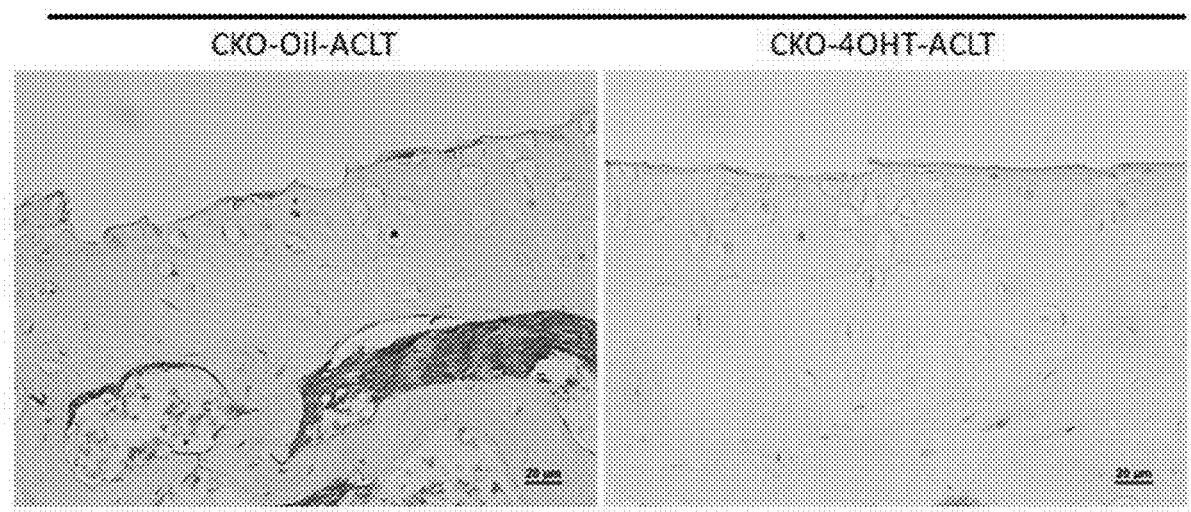
FIG. 6D shows the IHC staining of the tibial articular cartilages of the CKO-Oil-ACLT mice and the CKO-4OHT-ACLT mice, to observe the expression of the collagen type X, and determine the condition of the cartilages terminal differentiation.

The mammalian target of rapamycin (mTOR) is an important regulator of cell growth and proliferation. It was shown that the overexpression of mTOR is closely related to the inhibition of autophagy and the enhanced apoptosis of chondrocytes, and thus is also associated with the progression of cartilage degradation in OA. Constitutive autophagy of the chondrocytes may prevent cartilage degeneration, and thus is important in maintaining chondrocytes survival. As shown in FIG. 6C, the articular cartilage of tibia of the CKO-Oil-Sham mice, the CKO-Oil-ACLT mice, and the CKO-4OHT-ACLT mice was observed by using immunohistochemical staining (IHC), and it was seen that the CKO-4OHT-ACLT mice have a tendency of decreased mTOR expression. The decreased expression of mTOR represents an increased autophagy, which may cause a reduced occurrence of OA. In addition, the expression of the collagen type X of tibia articular cartilage in the CKO-Oil-ACLT mice and the CKO-4OHT-ACLT mice was observed by using IHC staining. The collagen type X is a representative marker for cartilage terminal differentiation, and a non-microfiber-forming collagen specifically synthesized by cells in the hypertrophy zone of the cartilage. Based on the current knowledge of degenerative arthritis, it is believed that the collagen type X will positively increase with the disease. Therefore, by observing the expression of the collagen type X, it can be established that the knockout of DDR1 can effectively relieve arthritis. As the expression of the collagen type X shown in FIG. 6D, compared with the CKO-Oil-ACLT control group, it was found that the CKO-4OHT-ACLT mice group exhibited inhibition of the cell proliferation in the hypertrophy zone and the reduced expression of the collagen type X in articular cartilage. In the CKO-4OHT-ACLT mice, the decreased apoptosis in the chondrocytes, the decreased mTOR expression, and inhibition of the collagen type X secreted by the cells in the hypertrophy zone were observed, which indicate that the maintenance of autophagy in chondrocytes is facilitated, and this may prevent the chondrocytes in ACLT-OA mice from dying and protect articular cartilage by maintaining a certain amount of cartilage to relieve arthritis.

Figure 7:
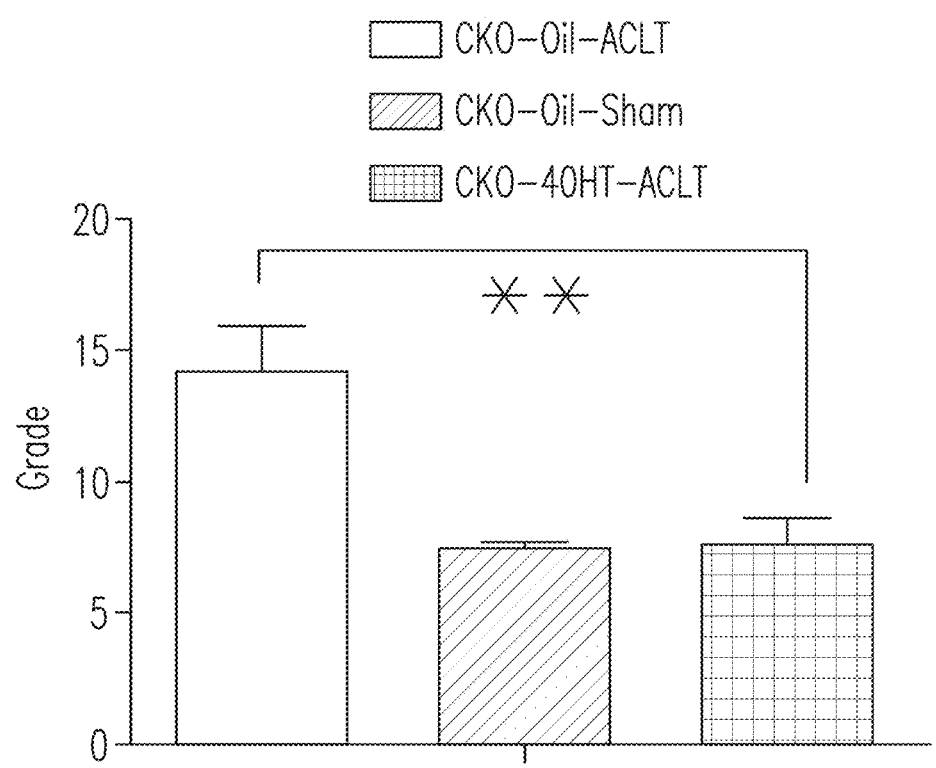
FIG. 7 shows the results of scoring the CKO-Oil-Sham mice, the CKO-Oil-ACLT mice and the CKO-4OHT-ACLT mice with the Osteoarthritis Research Society Internationale (OARSI) valuation system (N=5).

Osteoarthritis Research Society International (OARSI) is used to analyze the degree of damage to articular cartilage or OA severity, and the analysis results for CKO-Oil-Sham mice, the CKO-Oil-ACLT mice and the CKO-4OHT-ACLT mice are shown in FIG. 7. As shown in FIG. 7, the scores of CKO-4OHT-ACLT mice are similar to those of the CKO-Oil-Sham normal mice. It can be confirmed again by the quantitative results that the chondrocyte-specific knockout of Ddr1 in adult mice (CKO-4OHT-ACLT) can protect articular cartilage and effectively reduce the occurrence of degenerative arthritis.

From the results in FIGS. 3A to 7, it was found, by the ACLT-induced OA standard mouse model, that the Ddr1-knockout ACLT mice (CKO-4OHT-ACLT mice) showed a tendency to reduce degenerative arthritis. In detail, the Ddr1-knockout CKO-4OHT-ACLT mice had less wear on the surface of joint cartilage and a reduced sGAG, and showed phenomenons of inhibiting collagen type X secretions from the cells in the hypertrophy zone in articular cartilage and the decreased apoptosis of chondrocytes. The functional tests (running test and weight-bearing test) for Ddr1-knockout CKO-4OHT-ACLT mice also showed that compared to the CKO-Oil-ACLT normal mice, the CKO-4OHT-ACLT mice had better running ability and weight-bearing ability. In addition, the quantitative results of the OARSI score sheet for judging OA severity confirmed that the Ddr1-knockout CKO-4OHT-ACLT mice were less likely to have degenerative arthritis. The above results show that the inhibition of the expression and function of DDR1 in chondrocytes is helpful in preventing or treating degenerative arthritis, which is a new use that cannot be expected from the existing knowledge of DDR1 function in the prior art.

Although DDR1 and DDR2 belong to the same family, DDR1 mainly promotes the degradation and apoptosis of chondrocytes, while DDR2 mainly promotes the overexpression of MMP-13 in chondrocytes. Therefore, DDR1 and DDR2 are different in the mechanisms of regulating chondrocytes. Therefore, the various effects mentioned above that can be achieved by suppressing DDR1 in chondrocytes cannot be expected by any known DDR2 related mechanisms and functions. That is to say, the use of DDR1 inhibitor in preventing and treating joint arthritis, especially degenerative arthritis, cannot be derived from any known function of DDR2.

II. Activation of DDR1 Can Be Used to Prevent and Treat Abnormalities of Endochondral Ossification-Related Diseases.
1. Materials and Methods In the relevant experiments in Part II, mice were divided into the following three groups: (1) CKO mice intraperitoneally injected with oil (hereinafter referred to as "CKO-Oil mice", which is the control group), (2) Ddr1$^{flox/flox}$ transgenic mice intraperitoneally injected with 4-OHT (hereinafter referred to as "FF-4OHT mice", which is the control group), and (3) CKO mice intraperitoneally injected with 4-OHT (hereinafter referred to as "CKO-4OHT mice"). Each group at each time point N≥6. With regard to the experiments in Part II, the materials and methods that are the same as those in Part I are not repeated.

In Part II, the chondrocytes-specific Ddr1-deficient mice (A1(II)collagen-Cre/-Ddr1$^{flox/flox}$ mice) model is used, and thereby the role of DDR1 in bone development and cartilage development can be specifically explored.

Double Staining of Alizarin Red and Alcian Blue:

1-week-old, 2-week-old, 4-week-old and 8-week-old mice were euthanized with $CO_2$. Skins and internal organs were removed from the samples, and then the sample was fixed in 95% ethanol. Then, the sample was stained with 2% Alcian blue (Alcian Blue 8GX, A5268, Sigma-Aldrich) for 2 to 3 days until the cartilage matrix of the skeleton became blue. The sample was washed with 0.5% KOH (60377, Sigma-Aldrich, LLC, Taiwan) for one month until the muscles became transparent. The sample was washed by indistillation-distillation water for 2 days and then immersed in 1% alizarin red S (A5533, Sigma-Aldrich) for 15 minutes so that the mineralized bones were stained red. The sample was washed with KOH until the muscles became completely transparent, and then observed under a microscope.

Micro Computed Tomography (Micro-CT)

Mouse tibia was scanned and 3-D reconstructed by using a High resolution micro computed tomography (micro-CT, Skyscan 1076; Skyscan NV, Kontich, Belgium). Tibia was scanned at the condition of a voltage of 44 kV, a current of 222 μA, an exposure time of 1150 ms, and a voxel size resolution of 9 μm without filters. 3-D images were reconstructed using a scale of 0-0.09 for analysis (NRecon version 1.6.1.7; Skyscan NV, Kontich, Belgium). 3-D morphometric parameters for the 2.0 mm region of the tibia ROI (4 mm circle; 100 slices) are calculated by using a direct three-dimensional method, including bone volume (BV, $mm^3$), bone volume density (BV/TV, %), bone thickness (μm), trabecular thickness (Tb.Th, μm), trabecular spacing (Tb.Sp, μm), trabecular number (Tb.N, $mm^{-1}$) and connectivity density (Con.D, $mm^{-3}$) of the cortical bone.

Tissue Morphology Analysis By H&E Staining and Safranin O/Fast Green Staining

The collected tibia was fixed with 10% formalin solution, decalcified in 1% formic acid solution at 4° C., embedded in paraffin and then cut into slices of 5 μm thickness. The slices were stained with the hematoxylin (H3136, Sigma-Aldrich) and the eosin (318906, Sigma-Aldrich) for histological analysis, or stained with 0.1% Safranin O (HT90432, Sigma-Aldrich) and 0.05% Fast Green (FCF, 2353-45-9, Sigma-Aldrich) for detecting GAG under a microscope.

TUNEL Assay

The collected tibia was fixed with 10% formalin solution, decalcified in 1% formic acid solution at 4° C., embedded in paraffin and then cut into slices of 5 μm thickness. Apoptotic cells are detected by using in situ cell death detection kit (ab206386, Abcam) according to the protocol provided in the commercial kit. To quantify TUNEL cells, the number of brown cells was counted by Tissue FAXS, and more than 3 replicates were performed per trial.

2. Double Staining Analysis Proved the Skeletal Dysplasia of the CKO-4OHT Mice with Ddr1 Deletion During the Development of the CKO-4OHT Mice.

Figure 8A:
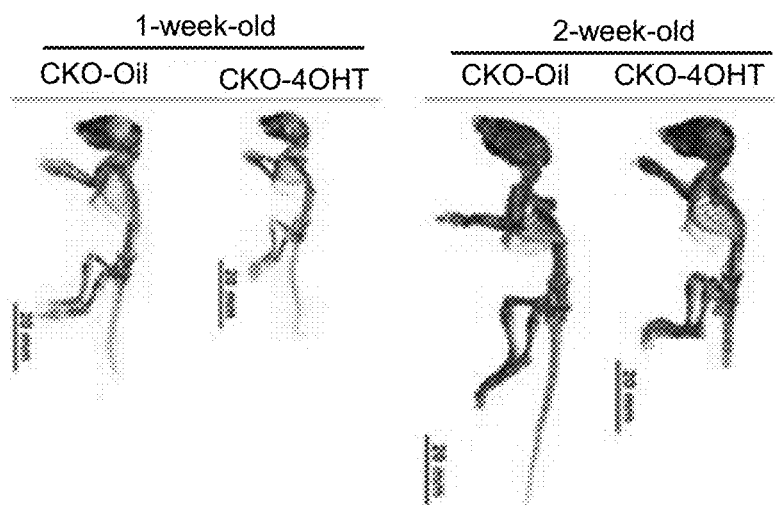
FIG. 8A shows the results of double staining of the CKO-4OHT mice and the CKO-Oil mice (the control group) of 1 week old and 2 weeks old by using Alizarin red and Alcian blue. Alizarin red can identify the location of the mineralized bone, while Alcian blue can be used to detect the proteoglycan in cartilage tissues.
Figure 8B:
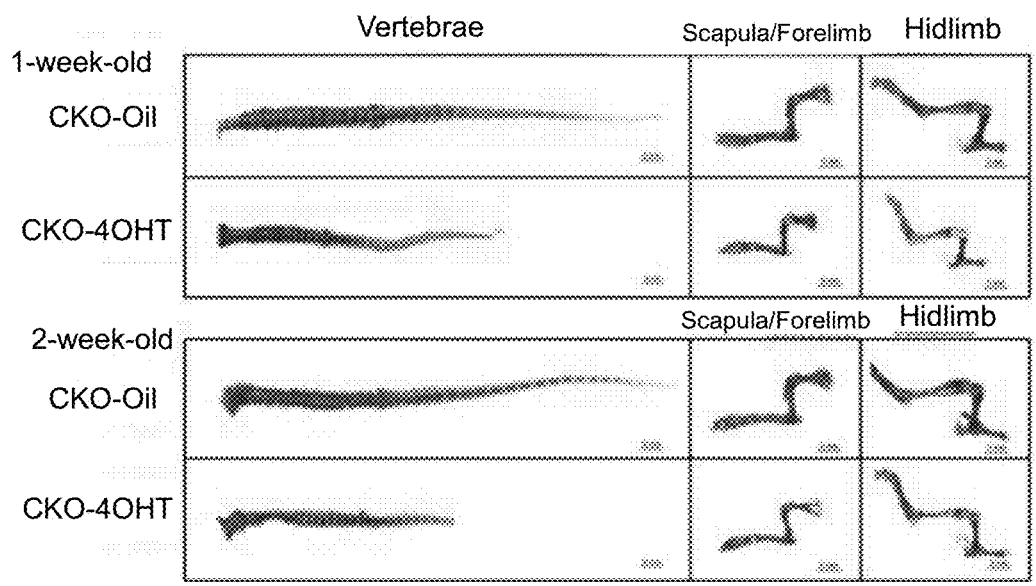
FIG. 8B shows the results of double staining of the vertebrae, scapula/forelimb and hind limbs of each group of mice in FIG. 8A.
Figure 8C:
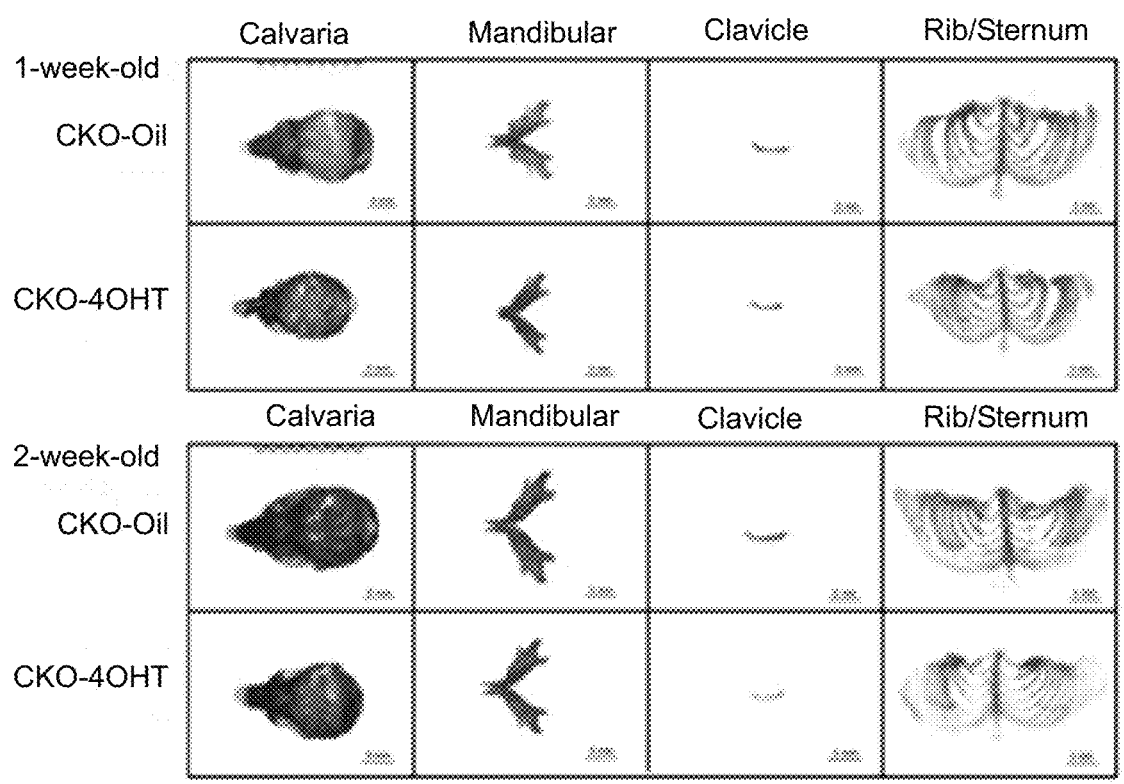
FIG. 8C shows the results of double staining of the calvaria, mandibular, clavicle and rib/sternum of each group of mice in FIG. 8A.

Histochemical analysis is often used to stain acidic polysaccharides such as cartilage and glycosaminoglycans in other body structures. In the results of Alcian Blue staining (also known as AB staining), the acidic polysaccharides around chondrocytes are dark blue or blue-violet, and the matrix is light blue. Referring to the AB staining results in FIG. 8A, in terms of appearance, no matter whether they are 1-week-old or 2-week-old mice, the body of the CKO-4OHT mice with Ddr1 deletion is significantly smaller than that of the CKO-Oil mice (the control group) of the same age. The results of the AB staining in FIGS. 8B and 8C show that in the long bones (such as the tibia, the femur, etc.), the cartilage distribution area, which is stained by Alcian Blue and thus is dark blue or blue-violet, of the CKO-4OHT mice is larger than that of the control group. In addition, after dismantling all joints, it can be observed that various bones of the CKO-4OHT mice were smaller and shorter than the control group, and this result showed that the ossification of the CKO-4OHT mice was incomplete. Actually, during the development, from 2-week-old to 10-week-old, of the CKO-4OHT mice, either the appearance or the bone components (including the clavicle, ribs, spine, upper limbs and lower limbs) showed a tendency of delayed growth and development.

3. The Knockout of Ddr1 in Chondrocytes Delays the Development of the Secondary Ossification Center in Femur and Tibia.

Figure 9A:
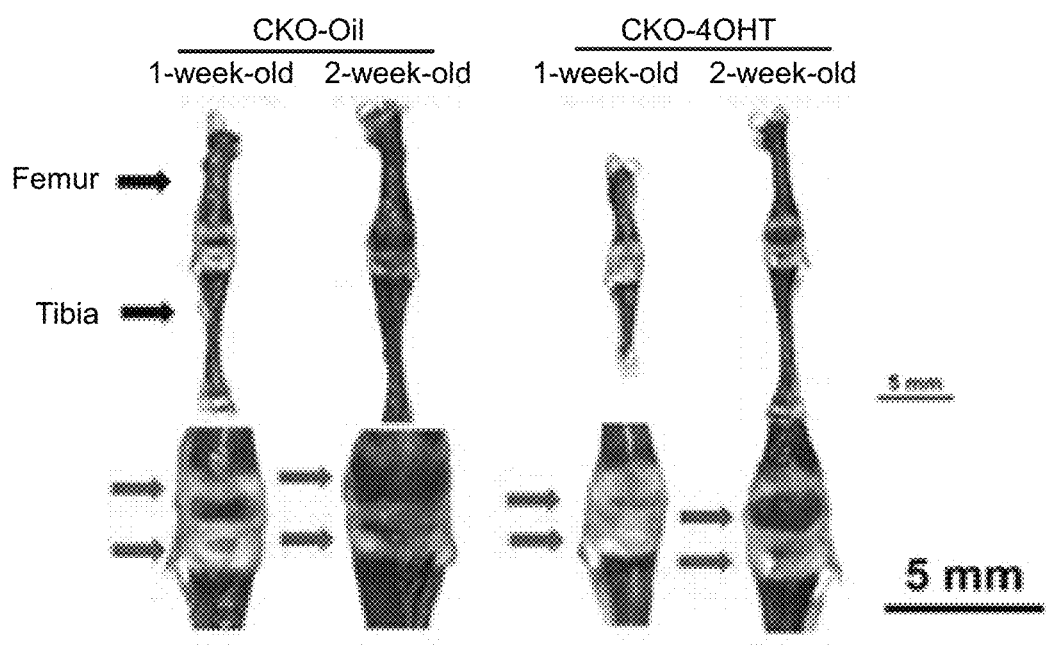
FIG. 9A shows the secondary ossification centers of the femur and tibia of the 1-week-old and 2-week-old CKO-4OHT mice and CKO-Oil mice (the control group) (wherein in the enlarged portion at the bottom of the figure, the upper arrow indicates the secondary growth zone of femur, and the down arrow indicates the secondary growth zone of the tibia).

During the development of bones, long bones (such as vertebrae, forelimb, metacarpal and hindlimb) are formed and developed through the endochondral ossification process, and in the long bones, a secondary ossification center is formed. FIG. 9A shows the secondary ossification centers of femur and tibia of the 1-week-old and 2-week-old CKO-4OHT mice and CKO-Oil mice (the control group), in which the upper arrow indicates the secondary growth zone of femur, and the lower arrow indicates the secondary growth zone of tibia. As shown in FIG. 9A, the secondary ossification center (as indicated by the arrow) in femur and tibia can be seen in the 1-week-old CKO-Oil mice (the control group), while in the 1-week-old CKO-4OHT mice, the secondary ossification center (as indicated by the arrow) is absent or the cells therein is dead, and the development of the secondary ossification center in the 2-week-old CKO-4OHT mice is also delayed. These results show that the knockout of Ddr1 in chondrocytes delays the development of the secondary ossification center in femur and tibia.

4. Endochondral Ossification of Tibia of the CKO-4OHT Mice is Delayed.

Figure 9B:
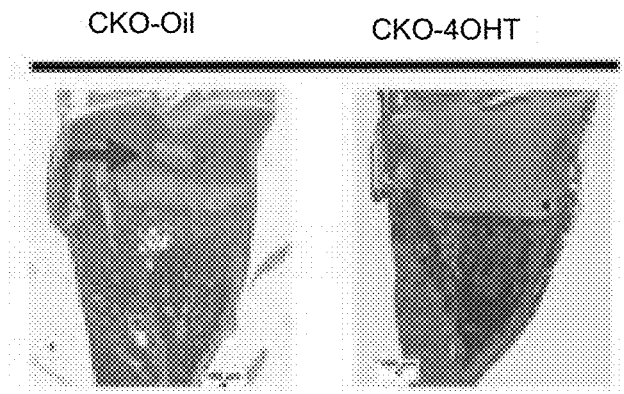
FIG. 9B shows the staining results of cartilage of the proximal tibia of the 1-week-old CKO-4OHT mice and the 1-week-old CKO-Oil mice (the control group) by using H&E staining. The arrow indicates the secondary ossification center.
Figure 9C:
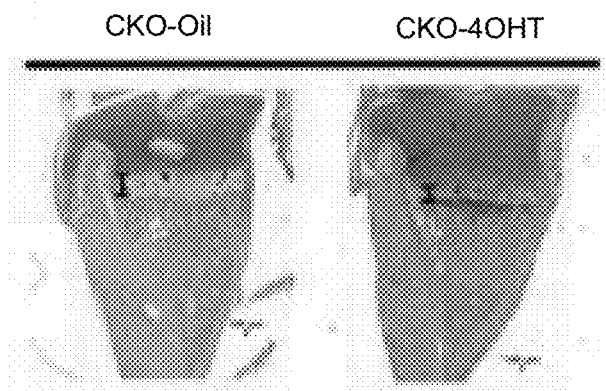
FIG. 9C shows the results of Safranin O/Fast Green staining of cartilage in the proximal tibia of the 1-week-old CKO-4OHT mice and the 1-week-old CKO-Oil mice (the control group). After staining, the proteoglycan (representing the cartilage area) is red, and collagen is blue. The I-shape black line shows the thickness of the hypertrophy zone of the proximal tibia of the CKO-4OHT mice and the CKO-Oil mice.

To evaluate the endochondral ossification during the development, tibia of the 1-week-old mice was collected, fixed with 10% formalin solution, embedded in paraffin, and then cut into slices having a thickness of 5 μm. The samples were stained with hematoxylin and eosin (H & E) and Safranin O/Fast Green. FIGS. 9B and 9C show the staining results of cartilage of the proximal tibia of the 1-week-old CKO-4OHT mice and CKO-Oil mice (the control group) by using hematoxylin and eosin (H&E) or Safranin O/Fast Green staining. In the proximal tibia of the 1-week-old CKO-4OHT mice, the region stained with Alcian Blue (the cartilage area) is significantly larger than that in the control group. Secondary ossification center (as shown by the arrow in FIG. 9B) can be clearly seen in the middle of the cartilage of the proximal tibia of the 1-week-old CKO-Oil mice, but no secondary ossification center was observed in the middle of the cartilage in the CKO-4OHT mice. The staining results of Safranin O/Fast Green are shown in FIG. 9C, in which the proteoglycan (representing the cartilage area) is red, and collagen is blue. The staining results of Safranin O/Fast Green show that the proximal tibia of CKO-4OHT mice had a denser sGAG staining (proteoglycan) and a longer cartilage region (red) than the CKO-Oil mice (the control group), which indicates that in the CKO-4OHT mice, the chondrocytes that synthesize proteoglycans in extracellular matrix may be more active than that in the CKO-Oil mice (the control group). In contrast, the hypertrophy zone in the proximal tibia of CKO-4OHT mice is smaller than the hypertrophy zone of the CKO-Oil mice (shown by the I-shape black line in FIG. 9C).

Figure 9D:
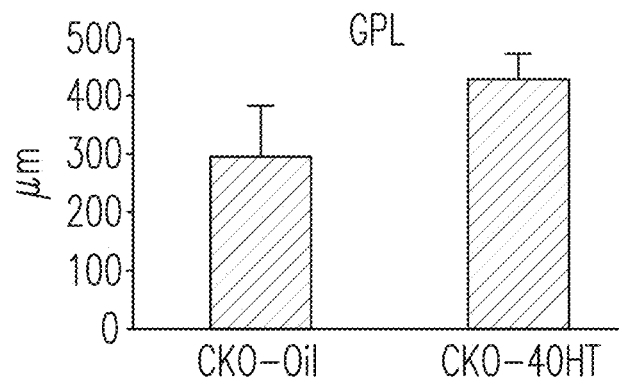
FIG. 9D shows the epiphyseal plate length (GPL) measured after staining of the tibia of the 4-week-old CKO-4OHT mice and the 4-week-old CKO-Oil mice (the control group) with Safranin O/Fast Green.
Figure 9E:
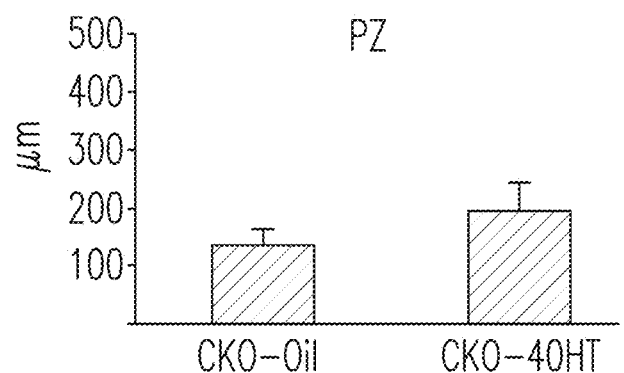
FIG. 9E shows the thickness of the proliferation zone (PZ) measured after staining of the tibia of the 4-week-old CKO-4OHT mice and the 4-week-old CKO-Oil mice (the control group) with Safranin O/Fast Green.
Figure 9F:
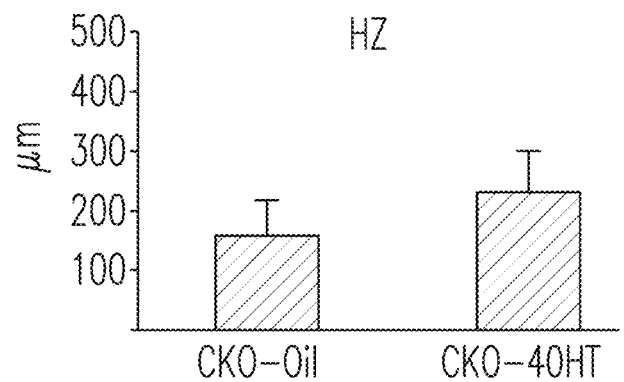
FIG. 9F shows the thickness of the hypertrophy zone (HZ) measured after staining the tibia of the 4-week-old CKO-4OHT mice and the CKO-Oil mice (the control group) with Safranin O/Fast Green.

FIGS. 9D to 9F show the epiphyseal plate length (GPL), the thickness of the proliferation zone (PZ) and the thickness of the hypertrophy zone (HZ) measured after staining the tibia of the 4-week-old CKO-4OHT mice and the CKO-Oil mice (the control group) with Safranin O/Fast Green. As shown in FIG. 9D, through further analysis of the epiphyseal plate, it was found that in the hypertrophy zone in the tibia of the 4-week-old CKO-4OHT mice, the length of the epiphyseal plate was increased and there were increased irregular cells.

Figure 10A:
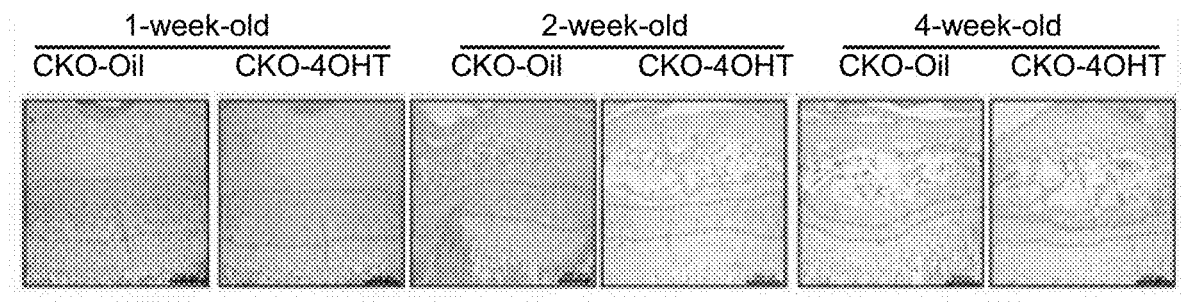
FIG. 10A shows Ki-67 immunohistochemical staining of the tibia epiphyseal plate in the 1-week-old, 2-week-old and 4-week-old CKO-4OHT mice and CKO-Oil mice (the control group) to observe the proliferation zone (which is between two dotted lines). Magnification is 100 times and the scale bar is 250 µm.
Figure 10B:
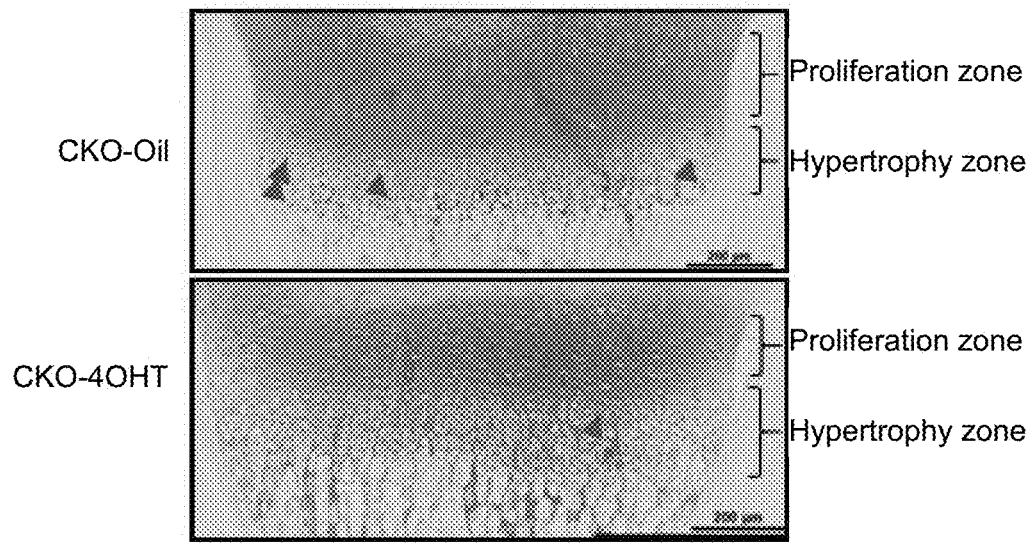
FIG. 10B shows the detection of apoptotic cells in the chondrocytes in the tibia epiphyseal plate of the 1-week-old CKO-4OHT mice and CKO-Oil mice by the TUNEL assay.
Figure 10C:
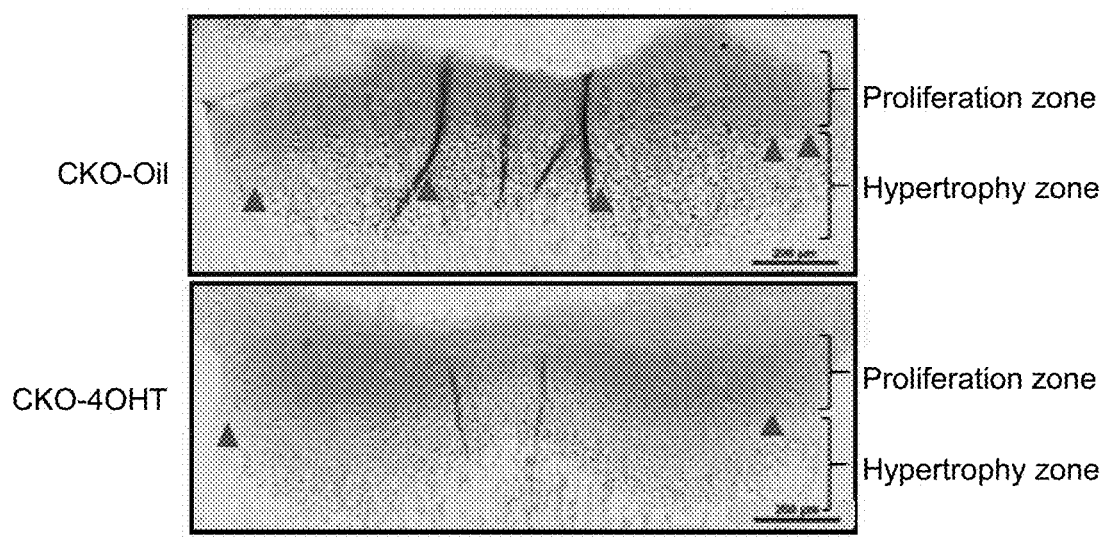
FIG. 10C shows the detection of apoptotic cells (as indicated by black dots) in the chondrocytes in the tibia epiphyseal plate of the 2-week-old CKO-4OHT mice and the 2-week-old CKO-Oil mice by the TUNEL assay.

Since more chondrocytes appear in the proliferative and hypertrophic regions, further analysis is performed to realize whether there is the increased proliferation, the decreased cell death, or both for the chondrocytes. Ki-67 immunohistochemical staining can be used to assess the percentage of total proliferating cells at all active phases of the cell cycle. Referring to the proliferation zone between the two dotted lines shown in FIG. 10A, the Ki67 staining revealed that, compared to the 1-week-old to 4-week-old CKO-Oil mice, there is less staining in the proliferation zone in the tibia epiphyseal plate of the CKO-4OHT mice. That is, there is a sharper decrease in the progression zone of the CKO-4OHT mice than that in the proliferation zone of the CKO-Oil mice. This result indicates that the increased chondrocytes in the epiphyseal plate of the CKO-4OHT mice are not derived from the proliferation that occurred in the proliferation zone. Therefore, the inventors examined apoptosis by the TUNEL assay that detects the DNA fragments by labeling nucleic acid ends, thereby evaluating the death of chondrocytes. FIG. 10B and FIG. 10C show the detection of apoptotic cells (shown by black dots) in the epiphyseal plate of the tibia of the 1-week-old and 2-week-old CKO-4OHT mice and CKO-Oil mice, respectively, by using the TUNEL assay. As can be seen from the detection results of the 2-week-old mice in FIG. 10C, the TUNEL staining in the hypertrophy zone of the CKO-4OHT mice was less than that in the CKO-Oil mice (as indicated by the arrows in FIG. 10C). As can be seen from FIGS. 10A to 10C, the knockout of Ddr1 reduces terminal differentiated chondrocytes during bone development.

The endochondral ossification is regulated by the feedback loop, including parathyroid hormone-related protein (PTHrP), Indian hedgehog (Ihh) and Bcl-2 JTHrP in the epiphyseal plate, which maintain the function of proliferating chondrocytes and inhibit the differentiation of chondrocytes into hypertrophy cells. The cartilages of the 4-5-day-old CKO-4OHT mice and CKO-Oil mice were obtained to detect the expression of Collagen type X, Ihh protein and PTHrP gene.

Figure 11A:
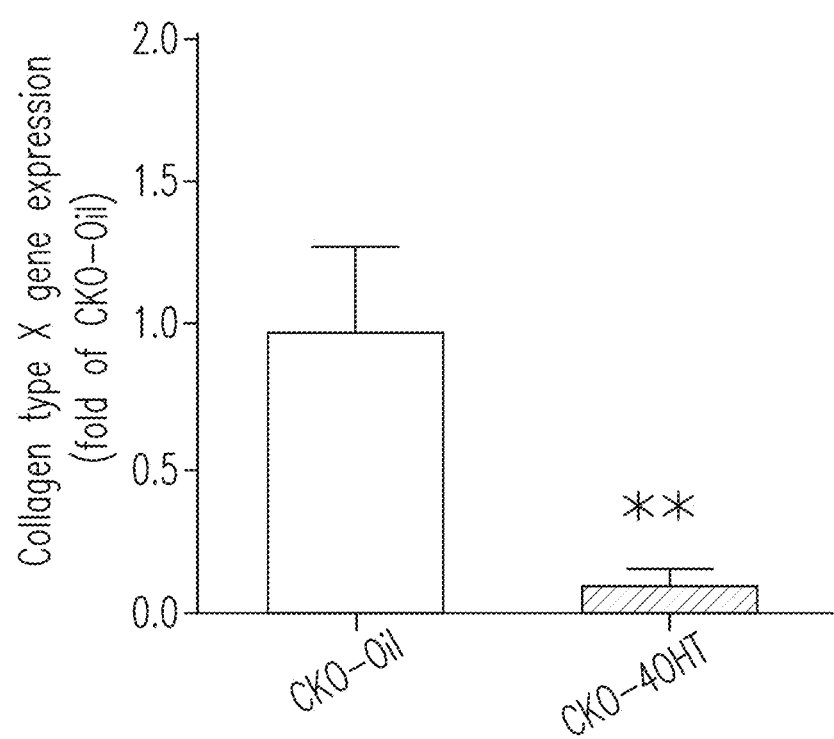
FIG. 11A shows the expression of the collagen type X gene in cartilages of the CKO-4OHT mice and the CKO-Oil mice 4-5 days after birth. ** indicates $p<0.01$ as compared to the CKO-Oil group.

The relative amount of mRNA was calculated by the cycle threshold (Ct) value of each PCR product and normalized to the level of GAPDH using the comparative Ct method. The relative value of the gene expression of the control CKO-Oil mice was set to 1 and all other amounts were converted to ratios. As shown in FIG. 11A, the collagen type X of CKO-4OHT mice was significantly reduced as compared to the collagen type X of the CKO-Oil mice. Furthermore, as compared to the CKO-Oil mice, the Ihh gene expression of CKO-4OHT mice was significantly reduced while the PTHrP gene expression of CKO-4OHT mice was significantly increased to more than four times (not shown).

Figure 11B:
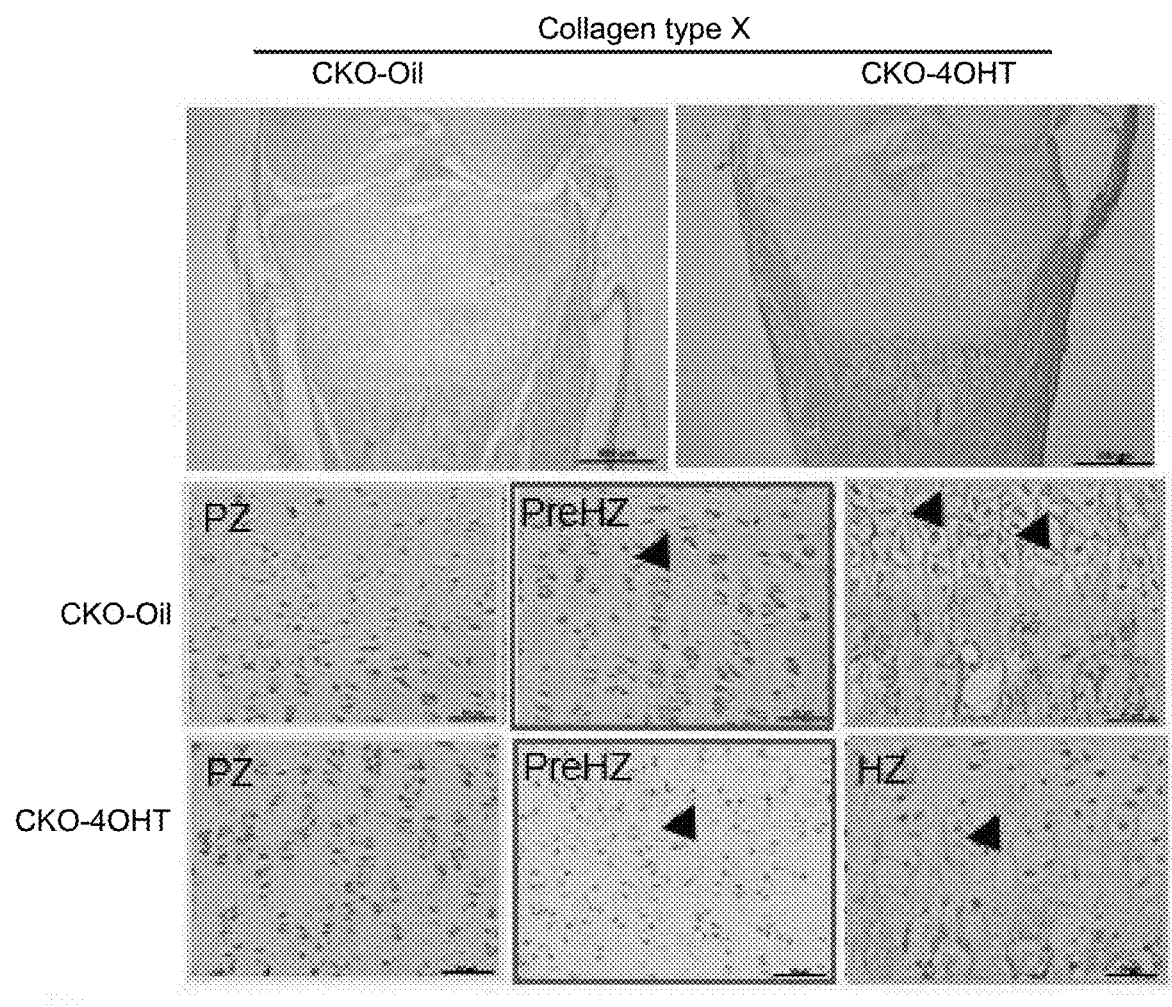
FIG. 11B shows the staining results of the tibia of the 1-week-old CKO-4OHT mice and the 1-week-old CKO-Oil mice by using immunohistochemistry staining and counterstaining with hematoxylin, which are observed under a microscope. PreHZ represents the pre-hypertrophic zone; HZ represents the hypertrophy zone; PZ represents the proliferation zone; and the arrows indicate the chondrocytes.

FIG. 11B shows the immunohistochemistry staining of the tibia of the 1-week-old CKO-4OHT mice and the CKO-Oil mice. Collagen type X is a chondrogenesis marker of the cartilage extracellular matrix. It can be seen from FIG. 11B that the collagen type X stain in proliferation zone (HZ) of CKO-4OHT mice can reduce the extracellular matrix of the pre-proliferation zone (PreHZ) (as indicated by the arrow) and the chondrocytes (as indicated by the arrow). In view of the fact that Ihh will feedback control the release of PTHrP during the endochondral ossification, the Ihh staining showed that the expression in the hypertrophy zone of CKO-4OHT mice was significantly lower than that of the control group (not shown). In addition, PTHrP in the proliferation zone of CKO-4OHT mice was increased (not shown). From the above, it was found that the collagen type X staining in the CKO-4OHT group mice was less than that for the 2-week-old CKO-Oil mice. These results indicate that the knockout of Ddr1 may delay the terminal differentiation of chondrocytes in the proliferation zone, which in turn leads to a delay in the endochondral ossification of the tibia of the 4-OHT-injected mice of the CKO-4OHT group. Furthermore, the length of the epiphyseal plate in the CKO-4OHT mice increased due to less chondrocyte apoptosis and no increase in proliferating cells. As a result, the chondrocytes in the epiphyseal plate of the CKO-4OHT mice had less apoptosis and less terminal differentiation.

5. Quantification of Skeletal Dysplasia of Tibia of the Cko-4OHT Mice Using Micro Computed Tomography (Micro-CT).

Figure 11C:
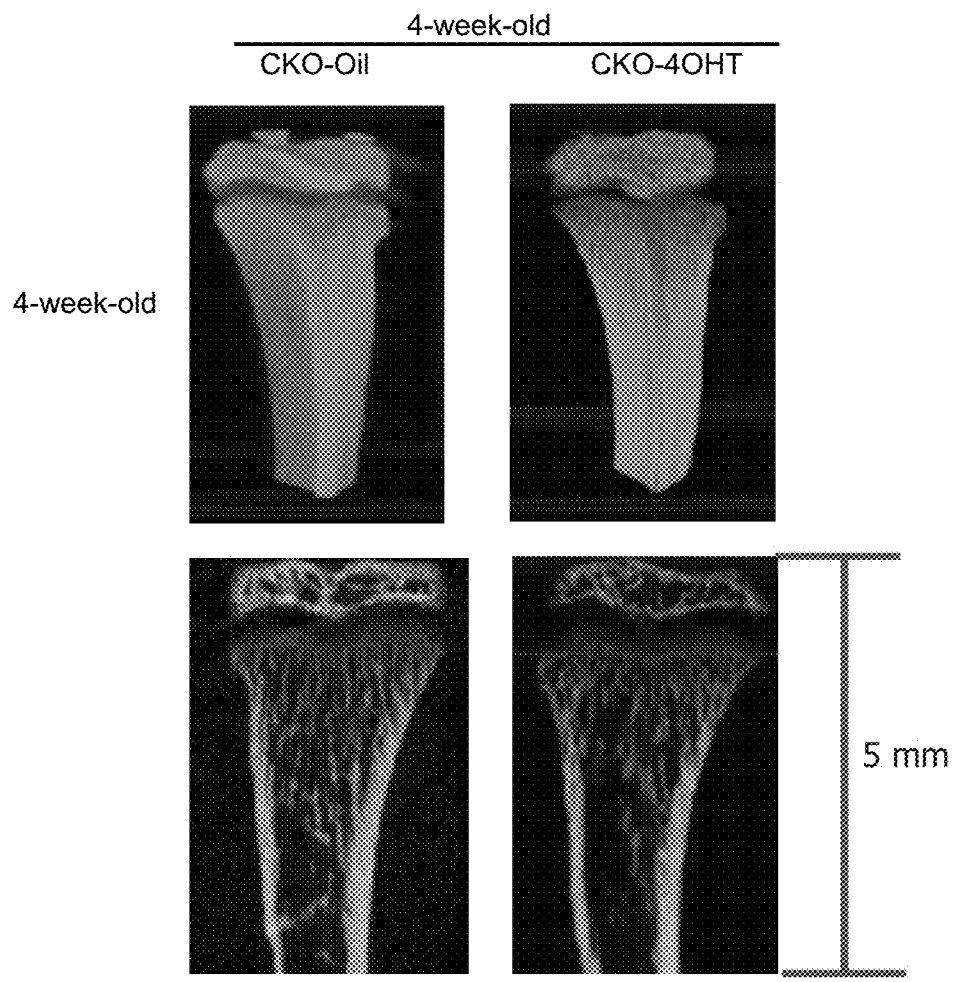
FIG. 11C shows the three-dimensional skeletal structure of the tibia of the 4-week-old CKO-4OHT mice and the 4-week-old CKO-Oil mice (the control group) observed using micro CT (micro computed tomography) with high-resolution. The upper two figures show three-dimensional views, and the lower two figures are cross-sectional views.
Figure 11D:
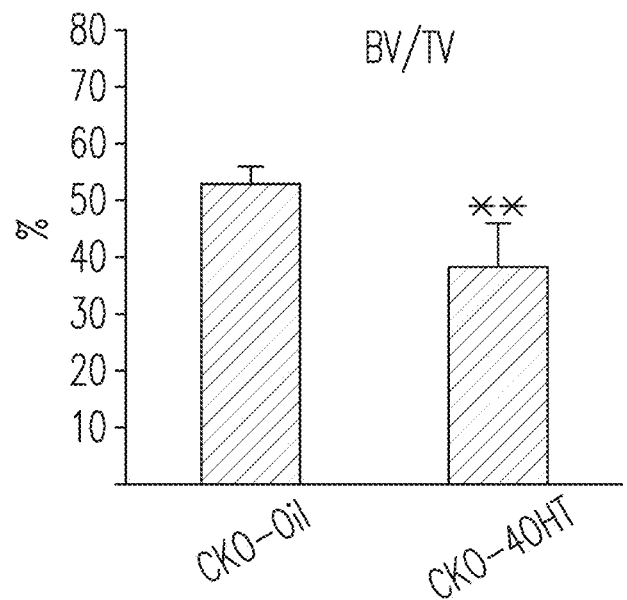
FIG. 11D shows the bone volume/total volume (BV/TV, %) of the cortical bone of the tibia in the 4-week-old CKO-4OHT mice and the 4-week-old CKO-Oil mice (the control group).
Figure 11E:
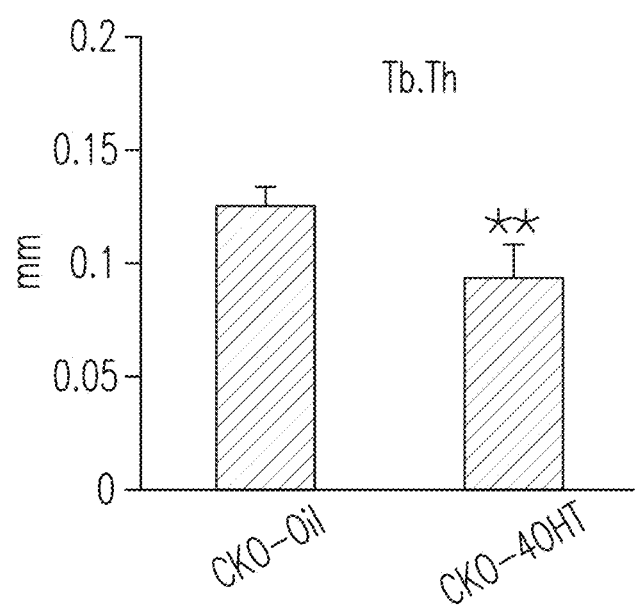
FIG. 11E shows the trabecular thickness (Tb.Th) of the tibia in the 4-week-old CKO-4OHT mice and the 4-week-old CKO-Oil mice (the control group).
Figure 11F:
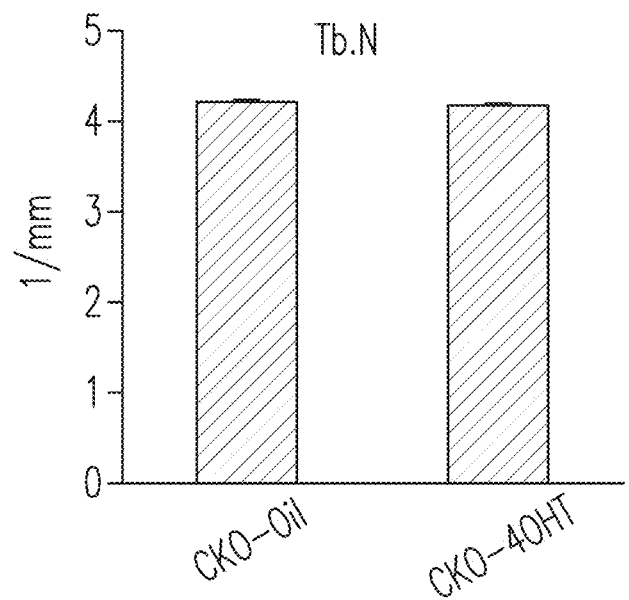
FIG. 11F shows the trabecular number (Tb.N) of the tibia in the 4-week-old CKO-4OHT mice and the 4-week-old CKO-Oil mice (the control group).
Figure 11G:
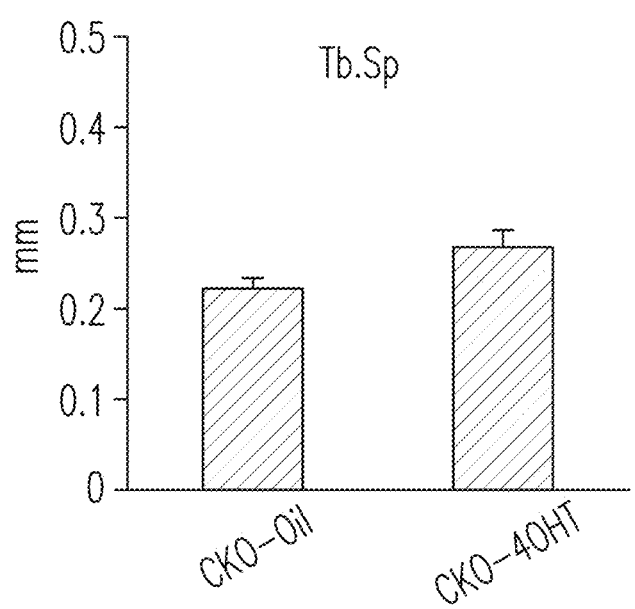
FIG. 11G shows the trabecular spacing (Tb.Sp) of the tibia in the 4-week-old CKO-4OHT mice and the 4-week-old CKO-Oil mice (the control group).

The three-dimensional micro-structures of the tibias of the 4-week-old CKO-4OHT mice and the CKO-Oil mice (the control group) were analyzed by using high resolution micro-CT, and the results are shown in FIG. 11C. The 3-D micro-CT images of the tibias were reconstructed and the 3-D morphological parameters were calculated. In tibia, the reconstructed 3-D images including the three-dimensional view (the top right part in FIG. 11C) and the cross-sectional view (the bottom right part of FIG. 11C) of the CKO-4OHT mice show that the size of the CKO-4OHT mice is smaller than that of the CKO-Oil mice (the control group). In addition, the average space for the tibia of the CKO-4OHT mice is reduced. As compared with the CKO-Oil mice (the control group), the tibia of the CKO-4OHT mice showed a significant decrease in the percentage of bone volume/total volume of the cortical bone (BV/TV, i.e., the bone volume density) and the trabecular thickness (Tb.Th), while there is no significant difference for the trabecular number (Tb.N) and the trabecular spacing (Tb.Sp) (as shown in FIG. 11D to FIG. 11G). It can be known from the above results that the knockout of the Ddr1 gene in chondroblasts reduced BV/TV and trabecular thickness, but did not affect the trabecular number and the trabecular spacing. The above evidences reveal that the knockout of DDR1 will make the structure of the bone more fragile and cause the issue of osteoporosis.

The experiments related to Part II show the following results (shown by FIG. 8A to FIG. 11G). During skeletal development, DDR1 positively regulates the function of chondrocytes during intramembranous ossification and endochondral ossification. The deletion of the Ddr1 gene in chondrocytes inhibits the degeneration of chondrocytes into hypertrophic chondrocytes and keep the chondrocytes to accumulate in the cartilage area without forming hard bones via calcification, which result in abnormalities of endochondral ossification (achondroplasia) and thus skeletal growth retardation. Therefore, DDR1 gene knockout can cause the dwarfism type mouse and the achondroplasia mouse with abnormalities of skeletal growth. Further mechanism investigation results show that the knockout of DDR1 inhibits chondrocyte degeneration, hypertrophy and apoptosis, which lead to abnormal bone development and achondroplasia. The experiment results reveal that DDR1 plays an important role in the early and late stages of bone and cartilage development. By regulating the associated pathways activating DDR1, it can be used to prevent or even treat bone abnormalities in dwarfism and achodroplasia. Since the expression of the normal Ddr1 gene (the control group) can cause the normal endochondral ossification to proceed and thus achondroplasia and skeletal growth retardation will not occur, the abnormalities of endochondral ossification and achondroplasia can be prevented or treated by gene therapy, preparation agents or preparation antibodies associated with the application of activating DDR1 pathway.

The present invention provides a use of Discoidin Domain Receptor 1 (DDR1) inhibitor in preparing a drug for preventing or treating osteoarthritis. The inhibition of DDR1 function can effectively slow the terminal differentiation and apoptosis of articular chondrocytes and then treat or prevent joint diseases, especially degenerative arthritis. The joint diseases include joint injury, anterior cruciate ligament injury, degenerative arthritis and the combinations thereof. Some examples of DDR1 inhibitors are described below, but DDR1 inhibitors are not limited to the listed examples. The aforementioned agents can be used alone or in combination with a common inhibitor.

In an embodiment, the DDR1 inhibitor can be a polynucleotide that hybridizes with a polynucleotide encoding a human DDR1 protein or its complementary strand and comprises at least 15 nucleotides. The polynucleotide of the present invention is preferably a polynucleotide that specifically hybridizes to the DNA encoding the polypeptide in the present invention. Such polynucleotides include probes, primers, nucleotides, and nucleotide derivatives (e.g., antisense oligonucleotides and ribozymes) that form a specific hybrid by hybridizing to the DNA encoding the polypeptide in the present invention or its complementary strands. The aforementioned antisense oligonucleotide is preferably at least 15 contiguous nucleotides corresponding to the DDR1 nucleotide sequence. The term "antisense oligonucleotide" as used herein means not only nucleotides that are completely complementary to a particular region of a DNA or mRNA, but also nucleotides having one or more mismatches, as long as the antisense oligonucleotide can specifically hybridize to the nucleotide sequence of DDR1.

The antisense oligonucleotide derivatives of the present invention acts on a cell which produces a polypeptide of the present invention by binding to a DNA or mRNA encoding the polypeptide in the present invention, inhibiting transcription or translation of the DNA or mRNA, promoting the mRNA degradation, inhibiting the expression of the polypeptide of the present invention, and thereby inhibiting the function of this polypeptide.

If necessary, the above derivatives can be formulated into tablets, powders, granules, capsules, microlipid capsules, injections, solvents, drops and freeze drying agents by adding excipients, isotonic agents, stabilizers, preservatives, analgesics, or the like. These can be formulated by well known methods.

The above antisense oligonucleotide derivative can be directly used in a patient's diseased site, or injected into a blood vessel to reach the diseased site. Antisense matrix (antisense-mounting medium) can also be used to increase persistence and film penetration, such as lipoproteins, poly-L-lysine, lipids, cholesterol, and lipofectin, or their derivatives.

In an embodiment, the DDR1 inhibitor can be a small interfering RNA (siRNA) comprising a combination of a sense nucleotide strand and an antisense nucleotide strand complementary to the DDR1 nucleotide sequence. siRNA is introduced into cells using standard techniques, including those that use DNA as a template to transcribe RNA. The above siRNA comprises polynucleotide including a sense nucleotide sequence and a antisense nucleotide sequence and encoding the human DDR1 protein. The siRNA is constructed such that a single transcript (double stranded RNA) has both a sense and complementary antisense sequence of the target gene, such as a hairpin. This method is used to alter the gene expression in cells, which means to readjust the expression level of DDR1. Binding of the siRNA to the DDR1 transcripts in the target cells results in a decrease in protein production in this cell. The oligonucleotide is at least 10 nucleotides in length and can be as long as the length of the natural transcript. Preferably, the oligonucleotide is 19-25 nucleotides in length. Most preferably, the oligonucleotide is shorter than 75, 50 or 25 nucleotides in length. The nucleotide sequences of the siRNAs can be designed by siRNA computer software well known to those skilled in the art.

The nucleic acid interference is widely valued by the pharmaceutical industry because of many specialities of nucleic acid interference. It can inhibit the expression of disease-associated proteins at the RNA level. This is different from most other drugs that function in protein. Traditionally, both the nucleic acid interference drugs and small molecule drugs belong to inhibitors, but the mechanism of action is different. Nucleic acid interference drugs play a role in inhibiting the expression of drug target genes, which not only has stronger targeting, but also hopes to produce more potential drugs, which can increase the inherent innovation advantages of nucleic acid interference therapy. Meanwhile, nucleic acid interference drugs can also be used in combination with traditional small molecule drugs and monoclonal antibody drugs in order to achieve better therapeutic effects.

In a preferred embodiment, the DDR1 inhibitor includes a compound of formula (I) or a pharmaceutically acceptable salt thereof:

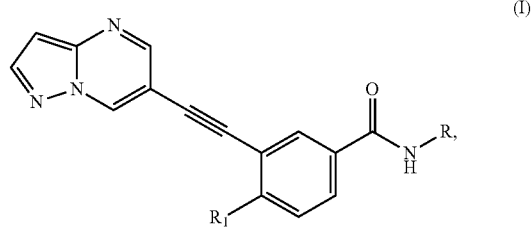

(I)

wherein R is one selected from the group consisting of

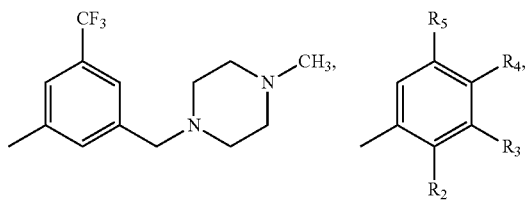

—CH(CH$_3$)$_2$, —(CH$_2$)$_3$CH$_3$, —CH$_2$CH(CH$_3$)$_2$, —C$_6$H$_{11}$ and —C$_5$H$_9$;
R$_1$ is one of —CH$_3$ and —CH$_2$CH$_3$;
R$_2$ is one selected from the group consisting of —H, —CH$_3$, —X and —OCH$_3$;
R$_3$ is one selected from the group consisting of —H, —CH$_3$, —X, —OCH$_3$, —CF$_3$, —OCH(CH$_3$)$_2$, —N(CH$_3$)$_2$,

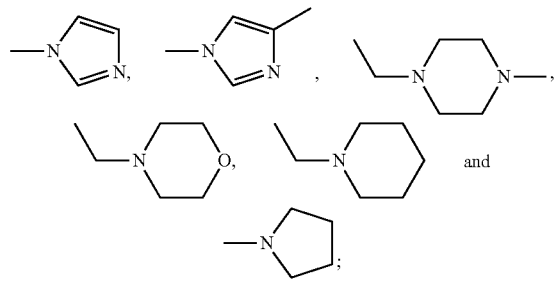

R$_4$ is one selected from the group consisting of —CH$_3$, —X, —OCH$_3$, —CF$_3$ and —H; and
R$_5$ is one selected from the group consisting of —CH$_3$, —X, —OCH$_3$, —CF$_3$ and —H, where X is a halogen.
In a preferred embodiment, DDR1 inhibitor is

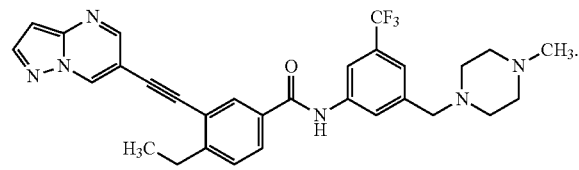 [SMILES: CCc1ccc(C(=O)Nc2cc(CN3CCN(C)CC3)cc(C(F)(F)F)c2)cc1C#Cc1cnc2ccnn2c1]

In an embodiment, the DDR1 inhibitor includes DDR1-specific inhibitory antibody, which may comprise a full length antibody, variable domains of the antibody, a Fab fragment, a Fab' fragment, an F(ab)2 fragment, an Fv fragment, a Fabc fragment, and/or a Fab fragment having a partial Fc domain.

The present invention also provides use of a DDR1 activator in preparing a medicament for preventing or treating abnormalities of endochondral ossification-related conditions. The medicament can prevent or treat abnormalities of endochondral ossification-related conditions by activating a DDR1-associated pathway. The abnormalities of endochondral ossification-related conditions include achondroplasia, hypochondroplasia, thantophoric dysplasia, dwarfism, and so on. Some examples of DDR1 activators are described below, but DDR1 activators are not limited to the examples listed. The aforementioned medicaments can be used alone or in combination with a coactivator.

In an embodiment, the DDR1 activator is a collage, in particular at least one of a collage type I to a collage type VI and a collage type VIII. Because the fibrillar collagens are DDR2 activators, not DDR1 activators, the aforementioned DDR1 activator preferably excludes fibrillar collagens, such as fibrillar collagen type I, fibrillar collagen type III, and fibrillar collagen type X.

In an embodiment, DDR1 activator is a DDR1-specific activating antibody, which may comprise a full length antibody, variable domains of the antibody, a Fab fragment, a Fab' fragment, an F(ab)2 fragment, an Fv fragment, a Fabc fragment, and/or a Fab fragment having a partial Fc domain.

An embodiment of the present invention provides a pharmaceutical composition comprising a DDR1 inhibitor or activator, wherein the pharmaceutical composition is optionally mixed with a pharmaceutically acceptable adjuvant or carrier. The pharmaceutical composition may additionally comprise other pharmaceutically active agents. In some embodiments, the pharmaceutical composition is formulated for administration: by inhalation, intraperitoneal, intravenous, intramuscular, subcutaneous, intracranial, intraventricular, oral, enteral, parenteral, intranasal, dermal, subcutaneous, topical, sublingual or transbuccal manner, or via catheter, via a lavage, via continuous infusion, via infusion, via inhalation, via injection, via local delivery, or via localized perfusion. In some embodiments, the pharmaceutical composition is formulated for oral administration. In some embodiments, the pharmaceutical composition is formulated as a unit dose.

The pharmaceutical composition in the present invention is in the form of a suitable preparation unit, which may be an oral solid preparation or an injection preparation. The oral solid preparation may be any one of a tablet, a capsule, a pill, and a granule. The administration preparation for injection can be any one of a water injection, a powder injection, and an infusion. The form of the preparation unit of the present invention is preferably an injection preparation, more preferably a small volume parenteral for injection or a powder injection.

In an embodiment, the pharmaceutical composition above can be administered alone or together with other agents, and the regime is performed according to the pharmacy routine method.

In an embodiment, the pharmaceutical composition above comprises a pharmaceutically acceptable carrier or medium, such as an excipient, a stabilizer, a solubilizer, an emulsifier, a suspending agent, a buffer, an isotonic agent, an antioxidant or a preservative, and the like. The following examples are given, but the present invention is not limited thereto, and a carrier or medium known in the art may be used. An excipient such as starch or lactose that does not have a pharmacological effect itself is preferable. The stabilizing agent comprises albumin, gelatin, sorbitol, mannitol, lactose, sucrose, trehalose, maltose, glucose, etc., preferably sucrose or trehalose. The solubilizer contains ethanol, glycerin, propylene glycol, polyethylene glycol, and the like. The emulsifier comprises lecithin, aluminum stearate or sorbitan sesquioleate. The suspending agent comprises polyethylene glycol, polyvinylpyrrolidone (PVP) or carboxymethylcellulose (CMC). The isotonic agents include sodium chloride, glucose, and the like. The buffer contains citrate, acetate, boric acid or phosphate. The antioxidant contains ascorbic acid, sodium hydrogen sulfite, sodium metabisulfite, and the like. The preservative contains phenol or the like.

The pharmaceutical composition comprising DDR1 inhibitor may additionally include a known agent commonly used in joint diseases, such as a treatment agent for articular disease, an anti-inflammatory agent, an analgesic agent, a bone regenerating agent, an osteoclastic inhibitor, an antibiotic or a growth agent. One or more of the above agents may be combined for use.

The treatment agents for articular disease may include articular cartilage extracellular matrix degradation inhibitor, a protecting agent of articular cartilage such as adrenal corticosteroid, chondoitin sodium sulfate, or hyaluronic acid (HA), or p21-activated kinase (PAK) inhibitor. The anti-inflammatory agents may include a steroidal anti-inflammatory agent or a non-steroid anti-inflammatory agent (NSAIDs), etc. The steroidal anti-inflammatory agents may include dexamethasone, cortisone, hydrocortisone, etc. The non-steroid anti-inflammatory agents may include aspirin, ibuprofen, naproxen, diclofenac, indomethacin, nabtomen, phenylbutazone, pyrazolone, etc. The analgesic agents may include NSAIDs, endorphin, dynorphine, enkephalin, codeine, dihydrocodeine, dextropropoxyphene, etc. The osteoclastic inhibitors may include an estrogen agent, calcitonin, and bisphosphonate. The antibiotics may include a penicillin antibiotic, a cephem antibiotic, an aminoglycoside antibiotic, a macrolide antibiotic, a tetracycline antibiotic, a peptide antibiotic, etc. The growth agents may include a bone morphogenetic protein (BMP), a bone growth factor (BGF), a platelet-derived growth factor (PDGF), a basic fibroblast growth factor (bFGF), an insulin, an insulin-like growth factor (IGF), or a transforming growth factor (TGF) etc.

The pharmaceutical composition in the present invention is preferably a targeting pharmaceutical composition, which may be delivered to a target cell, a target tissue or an organ at increased proportions relative to the blood circulation, lymphoid system, and other cells, tissues or organs. When this is achieved, the therapeutic effects of the targeting pharmaceutical composition is increased, while the scope and severity of the side effects and toxicity is decreased. When the drug is delivered in the form of a targeting pharmaceutical composition, the dosage at which the therapeutic effect can be achieved may be lower than that of the non-targeting pharmaceutical composition. Therefore, the medicament or pharmaceutical composition for treatment can be administered at a lower dose without detracting from its effectiveness, but at the same time reducing its side effects and toxicity.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for treating or alleviating a joint symptom associated with degenerative arthritis in a subject, comprising:
   identifying the subject having the degenerative arthritis; and
   administering to the subject an effective amount of a composition including a Discoidin Domain Receptor 1 (DDR1) inhibitor,
wherein the DDR1 inhibitor is

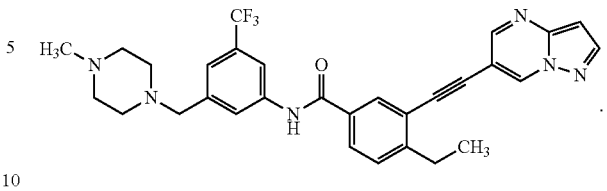

2. The method as claimed in claim 1, wherein the joint symptom is a joint disease.
3. The method as claimed in claim 2, wherein the joint disease is a degenerative joint disease.
4. The method as claimed in claim 3, wherein the degenerative joint disease is osteoarthritis.
5. The method as claimed in claim 3, wherein the degenerative joint disease is caused by a joint injury, an anterior cruciate ligament injury, or aging.
6. The method as claimed in claim 5, wherein the joint injury is at least one of a traumatic injury and a post-operative injury.
7. The method as claimed in claim 1, wherein the subject is a human subject.
8. The method as claimed in claim 1, wherein the DDR1 inhibitor is

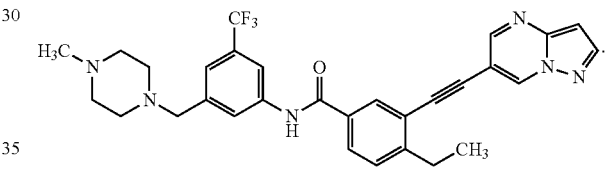

9. The method as claimed in claim 1, wherein the subject has a condition associated with increased levels of mammalian target of rapamycin (mTOR) and collagen type X.
10. The method as claimed in claim 9, wherein the condition associated with the increased levels of mTOR and collagen type X increases a potential development of at least one of a cartilage degradation and a chondrocyte death in the subject, and the administration of the composition inhibits, mitigates or alleviates the condition.
11. A method for treating or alleviating a degenerative joint disease in a subject, comprising:
    administering to the subject an effective amount of a composition including a Discoidin Domain Receptor 1 (DDR1) inhibitor for treating or alleviating the degenerative joint disease in the subject,
wherein the DDR1 inhibitor is

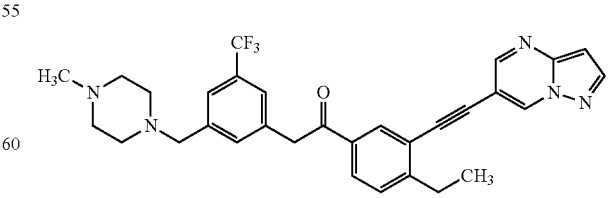

12. The method as claimed in claim 11, wherein the subject has an articular cartilage damage.
13. The method as claimed in claim 11, wherein the degenerative joint disease is osteoarthritis.

14. A method for reducing, inhibiting, mitigating or alleviating at least one of a cartilage degradation and a chondrocyte death in a subject suffering therefrom, comprising:
   administering to the subject an effective amount of a Discoidin Domain Receptor 1 (DDR1) inhibitor, thereby reducing, inhibiting, mitigating or alleviating the at least one of the cartilage degradation and the chondrocyte death in the subject,
   wherein the DDR1 inhibitor is

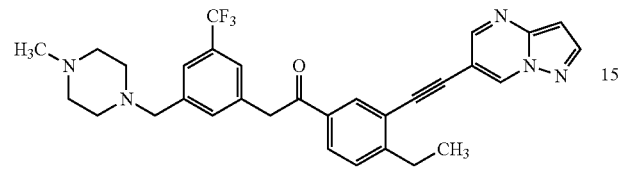

15. The method as claimed in claim 14, wherein the subject has a traumatic injury to cartilage tissues.

16. The method as claimed in claim 14, wherein the DDR1 inhibitor specifically or preferentially inhibits DDR1 activity.

* * * * *